(12) United States Patent
Raguin et al.

(10) Patent No.: US 8,317,325 B2
(45) Date of Patent: Nov. 27, 2012

(54) APPARATUS AND METHOD FOR TWO EYE IMAGING FOR IRIS IDENTIFICATION

(75) Inventors: Daniel H. Raguin, Acton, MA (US); James L. Cambier, Jupiter, FL (US)

(73) Assignee: Cross Match Technologies, Inc., Palm Beach Gardens, FL (US)

( * ) Notice: Subject to any disclaimer, the term of this patent is extended or adjusted under 35 U.S.C. 154(b) by 527 days.

(21) Appl. No.: 12/290,564

(22) Filed: Oct. 31, 2008

(65) Prior Publication Data

US 2010/0110374 A1    May 6, 2010

(51) Int. Cl.
*A61B 3/14*      (2006.01)
*A61B 3/10*      (2006.01)

(52) U.S. Cl. .......................... 351/206; 351/205
(58) Field of Classification Search ........... 351/200–246
See application file for complete search history.

(56) References Cited

U.S. PATENT DOCUMENTS

| | | | | |
|---|---|---|---|---|
| 4,641,349 A | 2/1987 | Flom et al. | ..... | 382/117 |
| 5,291,560 A | 3/1994 | Daugman | ..... | 382/117 |
| 5,471,542 A | 11/1995 | Ragland | ..... | 382/128 |
| 5,572,596 A | 11/1996 | Wildes et al. | ..... | 382/117 |
| 5,583,575 A | 12/1996 | Arita et al. | | |
| 5,642,170 A | 6/1997 | Hackett et al. | | |
| 5,751,836 A | 5/1998 | Wildes et al. | ..... | 382/117 |
| 5,978,023 A | 11/1999 | Glenn | | |
| 6,208,382 B1 | 3/2001 | Glenn | | |
| 6,247,813 B1* | 6/2001 | Kim et al. | ..... | 351/206 |
| 6,266,093 B1 | 7/2001 | Glenn | | |
| 6,526,160 B1* | 2/2003 | Ito | ..... | 382/117 |
| 6,652,099 B2 | 11/2003 | Chae et al. | | |
| 6,985,126 B2 | 1/2006 | Hoppenbrouwers et al. | | |
| 7,027,018 B2 | 4/2006 | Nitta et al. | | |
| 7,034,453 B2 | 4/2006 | Kai et al. | | |
| 7,038,651 B2 | 5/2006 | Nitta et al. | | |
| 7,046,262 B2 | 5/2006 | Feng et al. | | |

(Continued)

FOREIGN PATENT DOCUMENTS

CN         2535823        2/2003

(Continued)

OTHER PUBLICATIONS

"Information technology—Biometric data interchange formats—Part 6: Iris image data", ISO/IEC 19794-6, International Organization for Standardization, Geneva, Switzerland, 2005.

(Continued)

*Primary Examiner* — Mohammed Hasan
(74) *Attorney, Agent, or Firm* — Kenneth J. Lukacher

(57) ABSTRACT

The apparatus represents a device having one or two sensors for capturing a single image or two images having the subject's eyes, and processor(s) in a housing with the one or two sensors and/or in a computer system which receives the single image or two images. Such processor(s) determine a head tilt angle between a virtual line extending between the two eyes of the subject in accordance with a predefined features associated with the eyes and a dimension characterizing zero head tilt in the single image or two images, segment left and right iris images, and rotate the segmented left and right iris images in accordance with the angle to substantially remove head tilt when present. The apparatus may also determine head tilt using predefined features associated with a single eye in the image. The resulting iris image(s) are utilized for enrollment or identification.

51 Claims, 15 Drawing Sheets

U.S. PATENT DOCUMENTS

| | | |
|---|---|---|
| 7,248,720 B2 | 7/2007 | Muller et al. |
| 7,266,150 B2 | 9/2007 | Demos |
| 7,298,874 B2 | 11/2007 | Cho |
| 7,302,087 B2 | 11/2007 | Cho |
| 7,324,706 B2 | 1/2008 | Bassi |
| 7,593,550 B2 * | 9/2009 | Hamza ............ 382/117 |
| 7,756,301 B2 * | 7/2010 | Hamza ............ 382/117 |
| 7,801,335 B2 * | 9/2010 | Hanna et al. ........ 382/117 |
| 2002/0154794 A1 | 10/2002 | Cho ................ 382/117 |
| 2003/0006991 A1 | 1/2003 | De Haan et al. |
| 2003/0146885 A1 | 8/2003 | Hoppenbrouwers et al. |
| 2003/0160736 A1 * | 8/2003 | Faso et al. ............ 345/8 |
| 2004/0189680 A1 | 9/2004 | Feng et al. |
| 2005/0140825 A1 | 6/2005 | Kasahara et al. |
| 2005/0259064 A1 | 11/2005 | Sugino et al. |
| 2006/0018519 A1 | 1/2006 | Siegel et al. |
| 2006/0092113 A1 | 5/2006 | Nitta et al. |
| 2006/0158107 A1 | 7/2006 | Kai et al. |
| 2006/0158410 A1 | 7/2006 | Fujine |
| 2006/0176261 A1 | 8/2006 | Nitta et al. |
| 2006/0204042 A1 * | 9/2006 | Hammoud et al. ........ 382/107 |
| 2007/0201728 A1 | 8/2007 | Monro ............ 382/117 |
| 2007/0237365 A1 | 10/2007 | Monro ............ 382/115 |
| 2008/0097983 A1 | 4/2008 | Monro ............... 707/5 |
| 2008/0170759 A1 | 7/2008 | Monro ............ 382/117 |
| 2008/0170760 A1 | 7/2008 | Monro |
| 2008/0187183 A1 | 8/2008 | Monro |
| 2008/0253622 A1 | 10/2008 | Tosa et al. ............ 382/117 |
| 2009/0060348 A1 | 3/2009 | Monro |
| 2009/0092292 A1 | 4/2009 | Carver et al. |
| 2009/0169064 A1 * | 7/2009 | Kim et al. ............ 382/117 |

FOREIGN PATENT DOCUMENTS

| | | |
|---|---|---|
| EP | 1 751 695 B1 | 6/2008 |
| JP | 2002-351382 A | 12/2002 |
| TW | 2003-005128 | 3/1992 |
| TW | 2004-016436 | 3/1992 |
| TW | 2004-002673 | 12/1992 |
| TW | 2003-06745 A | 11/2003 |
| WO | WO 02/104005 A1 | 12/2002 |

OTHER PUBLICATIONS

Iris Image Interchange Format ANSI INCITS 379-2004.

Manual of Photogrammetry, 5th Edition, American Society of Photogrammertry and Remote Sensing, 1980.

O'Gorman, L., Sammon, M., and Seul, M., Practical Algorithms for Image Analysis, (Cambridge University Press, New York, NY) pp. 157-159, 182-185, 217-219, 2008.

Foley, J., van Dam, A., Feiner, S., and Hughes, J., Computer Graphics Principles and Applications, (Addison-Wesley, Reading MA), pp. 204-208, 1990.

Nandakumar, K., Chen, Y., Dass, S. C., and Jain, A. K., "Likelihood Ratio Based Biometric Score Fusion", IEEE Transactions on Pattern Analysis and Machine Intelligence, vol. 30, No. 2, pp. 342-347, Feb. 2008.

Chang, J., Cyclotorsion during laser in situ keratomileusis, Journal of Cataract and Refractive Surgery, 34(10):1720-1726, 2008.

Uzunova, V. I., An eyelids and eye corners detection and tracking method for rapid iris tracking, Master's Thesis, Otto-von-Guericke University of Magdeburg, Department of Computer Science, Magdburg Germany, 2005.

* cited by examiner

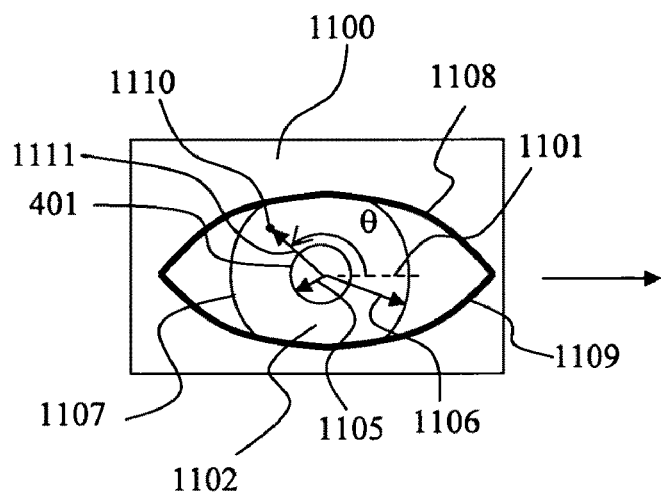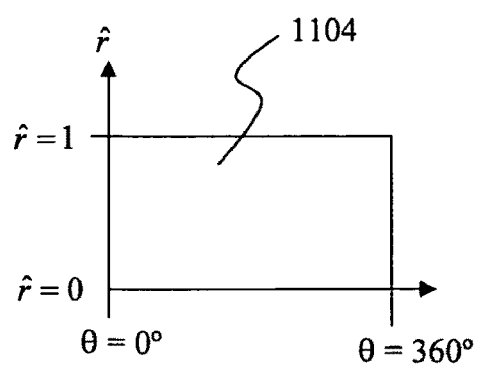
FIG. 11A  FIG. 11B
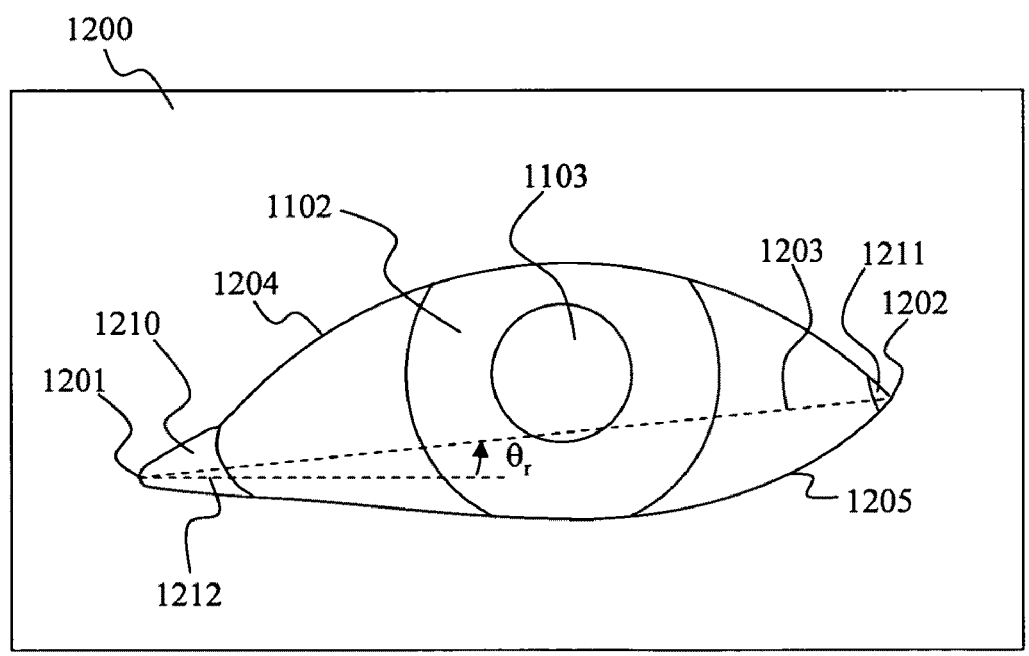
FIG. 12

APPARATUS AND METHOD FOR TWO EYE IMAGING FOR IRIS IDENTIFICATION

FIELD OF THE INVENTION

The present invention relates to an apparatus (or device) and method for imaging two eyes of a subject, and particularly to an apparatus and method for imaging the two eyes of a subject in which head tilt of the subject is substantially removed from left and right iris images utilizing either a single image of both eyes of the subject, or two images each of a different eye of the subject captured at or substantially the same time. Although preferably head tilt angle (or iris rotation) is determined and used to remove head tilt in iris images of two eyes of a subject, an apparatus and method is also described for determining head tilt angle using an image of a single eye, which may then be used to remove head tilt (or iris rotation) in an iris image segmented from such image. The invention further describes the use of iris images with substantially zero head tilt for enrolling or identifying a subject, or verifying a subject's identity. Interpupillary distance (IPD) or IPD-to-iris ratio may be determined and used to provide additional information for enrolling or identifying the person in an iris identification system.

BACKGROUND OF THE INVENTION

Existing iris recognition systems are based upon the use of images from a single eye in which a presented iris image is compared to a database of iris images of enrolled people. See for example, U.S. Pat. Nos. 4,641,349, 5,291,560, 5,572,596, and 5,751,836. However, each person at the time of iris image capture for identification typically may have his or her head tilted at a different angle than at the time of acquisition of the reference iris image used for enrollment, resulting in the presented iris image for identification being rotated at some unknown angle relative to the reference iris image. The head tilt problem results in extra processing to account for such unknown relative rotation, especially for large databases of enrolled people. It would be desirable to substantially remove head tilt in iris images by using information provided from both eyes at the time of enrollment and at a time when iris images are captured for identification to avoid such extra processing, and thereby result in faster identification. In addition to improving processing time, head tilt information provided from two eyes can improve spoof detection of a fake iris and improve the speed and accuracy of eyelid segmentation.

Although a two eye pickup unit is described in U.S. Pat. No. 6,247,813, the unit processes each eye separately, and does not account for iris rotation due to head tilt. Further U.S. Pat. No. 7,248,720 uses information in addition to iris images for identification, but is limited to the extraction of information from the iris and retina of a single eye. U.S. Pat. No. 6,652,099 describes an apparatus for capturing both irises of a person in images and using both imaged irises in an iris recognition system, where the distance between the iris images of the both eyes is reduced to eliminate the space between the eyes, making more effective use of the available CCD area. U.S. Pat. No. 6,652,099 describes in its background that iris rotation cannot be determined from a single eye, and that the degree of iris rotation is obtainable to reduce comparative search times in iris recognition, but does not describe a method for readily enabling the determination of the degree of iris rotation or substantially removing the iris rotation problem when people's iris images are enrolled in an iris recognition system. Furthermore, U.S. Pat. No. 6,652,099 neither accounts for head tilt and thus iris rotation, nor any calculated interpupillary distance in the imaged eyes as a parameter in an iris identification system when comparing iris information stored in a database.

Prior art has accounted for iris rotation by relative rotation of iris images by translation of normalized polar templates of an iris image. Thus, comparative searching is performed over relative rotations between each template of iris reference images and the template of a presented iris image in a range of expected relative rotation. As stated earlier, this is a time consuming computational process, especially for large databases of templates of iris reference images. For example, each of the reference templates may need up to seven relative rotations with the presented template. Further, such methods for accounting for iris rotation have been applied to images of a single eye. See, for example, U.S. Pat. Nos. 7,298,874, 7,302,087, and 5,291,560.

International standards for exchange of iris image information have been established. These standards specify data formats for storage and exchange of iris data that includes information about rotation angle, see "Information technology—Biometric data interchange formats—Part 6: Iris image data", ISO/IEC 19794-6, International Organization for Standardization, Geneva, Switzerland, 2005. However, such standard, like U.S. Pat. No. 6,652,099, does not relate to the removal of head tilt which caused the iris rotation angle in the first place at iris image capture at enrollment and for comparative searching.

SUMMARY OF THE INVENTION

Accordingly, it is a feature of the present invention to provide an apparatus for imaging two eyes of a subject, such as a person, for use in one of enrolling, identifying, or verifying the subject in an iris identification (or recognition) system utilizing iris images in which the head tilt which causes iris rotation is substantially removed in such iris images.

It is another feature of the present invention to provide an apparatus for imaging two eyes of a person using either one sensor array to capture a single image of both eyes of a subject, or two sensor arrays each capturing an image of a different eye of the subject at or approximately at the same time, in which head tilt is determined using a virtual line extending through locations of predefined features determined in different eyes in the image(s) and a horizontal axis representing zero head tilt with respect to the one or two sensor arrays.

It is another feature of the present invention to provide an apparatus for imaging the iris of two eyes of a subject and processing iris images of the eyes to determine IPD or IPD-to-iris ratio to reduce comparative search times in an iris identification system.

A further feature of the present invention is to provide an apparatus for imaging one or two eyes of a subject which facilitates the detection of false iris images.

A still further feature of the present invention is to provide an apparatus for imaging two eyes of a subject in which the positions of the upper eyelids located in each eye image(s) are determined and whether such positions are substantially the same or not indicates whether such determination of eyelid position is sufficiently accurate to allow proper segmentation of iris images therefrom.

A yet another feature of the present invention is to provide an apparatus for determining head tilt angle using an image of a single eye of a subject, which may then be used for enrolling, identifying, or verifying a subject in an iris identification (or recognition) system.

Briefly described, an apparatus embodying the present invention has a plurality of illumination sources for illuminating both eyes of a person, one or two sensor arrays which capture a single image or two images, respectively, representing the different eyes of a subject captured at or approximately at the same time, and at least one processor, in which when a single image is captured having both eyes of a subject, a dimension extends in the single image associated with zero head tilt, and when two images are captured each having a different eye of the subject, each of the sensor arrays is calibrated with respect to a common imaging plane to enable locations in images of different eyes of a subject captured by the sensor arrays to be related to coordinates along the common plane, and a dimension along the common plane is associated with zero head tilt. The processor determines a location of a predefined feature associated with each of the different eyes of the subject present in the captured single image or two images, in which when two images are captured the location of the predefined feature is determined in each of the images in coordinates along the common plane. The processor then determines an angle between a virtual line extending between the two eyes of the subject, in which the virtual line extends through the location of the predefined feature of each of the different eyes of the subject in the single image or two images, and the dimension associated with zero head tilt along the single image or the common plane, respectively. The processor segments the left and right iris images from the captured single image or two images of the different eyes of the subject, and then rotates the left and right iris images in accordance with the angle in a direction which substantially removes head tilt when present in the iris images, and thereby provide iris images of each of the eyes with substantially zero head tilt.

Additionally, each of one or more sensor arrays may have an optical system for imaging onto the sensor array. When two sensor arrays are present in the apparatus, the two sensor arrays are calibrated, via their respective optical system, along a common plane representing a target form (at or near where the eyes of a subject would be present to the sensor arrays) having features imaged by the two sensor arrays to provide two calibration images in which features on calibration images are calibrated to known coordinates along the target form to enable locations in images of different eyes of a subject captured by the sensor arrays to be related to coordinates along such common plane. If a single sensor array is present in the apparatus, and the optics of the optical system causes optical distortion in images captured by the sensor array which negatively affects desired accuracy of the tilt angle determination, it is preferably that the single sensor array is calibrated in the same manner as the two sensor arrays with respect to a common plane. In this case, the locations of predefined features, the virtual line determined, and the dimension associated with zero tilt are all in coordinates of the common plane, rather than the sensor array.

The predefined features may represent the pupil or iris center of each of the eyes, and thus the virtual line is an interpupillary line between the eyes. The processor may determine a distance along this interpupillary line, i.e., and thus the interpupillary distance (IPD) of the subject, between the location of the predefined features associated with each of the different eyes of the subject in coordinates of the common plane when established for the two sensor arrays (or single sensor array) representing actual object distances about the plane of the eyes perpendicular to the optical axis of the optical system of each of the one or more sensor arrays. IPD-to-iris ratio may also be determined by the processor, by the ratio of the distance between the location of the predefined features, such as the pupil or iris center, of each of the different eyes of the subject in the single image or two images in terms of image coordinates (or along the common plane as described above), and the outer diameter of each of the left and right irises in the captured single image or two images. As a different IPD-to-iris ratio may be produced for each of the eyes, a single IPD-to-iris ratio may be determined by dividing the IPD with the average of the outer iris diameters of the subject's eye. The IPD-to-iris ratio is useful when an absolute IPD cannot be measured, as in the case of a single sensor array which is not calibrated along a common plane representing actual spatial coordinates.

As stated above, the apparatus may have a single two-dimensional sensor array for capturing a single first image having both the left and right eyes of a subject, or may have two two-dimensional sensor arrays providing two images each having a different one of the left and right eyes captured at or approximately at the same time. When two sensor arrays are present, the time lag between the capture of the left and right second iris images is small enough (e.g., fraction of a second) such that any motion of the head, eye, and the sensor arrays and their optical systems relative to each other is minimal, and the accuracy of the determined virtual line (e.g., interpupillary line) is not compromised.

The apparatus may be provided in a housing having such one or two sensor arrays, optical system for each sensor array, and the illumination sources. The processor and memory accessible to the processor providing image processing described herein may be provided in the housing, or such processor may be external to the housing and coupled for data communication to receive and then process the two-dimensional array of pixels for each of the one or two first images. The processor may be part of a computer system, or other microprocessor-based system, for enabling iris identification, enrollment, and/or verification, in which the apparatus may be part of such iris identification system. The processor generates left and right templates representative of the left and right iris images, respectively, which are either stored for enrollment in a database of identification data having at least templates of left and right iris images with substantially zero head tilt of a plurality of subjects when the apparatus is used for enrollment of the subject, or the generated left and right iris templates are compared to each of the templates of left and right iris images stored in the database to determine scores representative of the amount of match to identify the subject, or the generated left and right iris templates are compared to one of the templates of left and right iris images stored in the database associated with inputted subject information to determine a score representative of whether the subject is verified or not. Although one processor is described, multiple processors may be provided and programmed to enable the described image processing described herein, and such processors may be present in the housing with the one or two sensor arrays, or the computer system, or both.

The database in addition to right and left templates may store IPD or IPD-to-iris ratio, if determined, and other personal information related to such templates, such as name, photograph of the individual, or other types of information typical of iris identification or recognition systems.

Comparative matching by the computer system in the database may be performed for the left and right irises separately, as described above, to provide a separate left iris score and right iris score for each comparison, or such scores may combined. Further, the left and right templates of the subject may be combined into a composite template in which the database stores similarly composite templates for comparison. The left and right iris images may be combined with each other and then a template of the combined image generated in which the database contains similarly stored templates based on combined left and right iris images for comparison. By using both right and left iris images known to come from the same person, the accuracy of recognition is enhanced.

A method for acquiring images of the eyes of a subject is also described having the steps of: capturing a single image or two images using a one or two sensor arrays, respectively, representing the different eyes of a subject captured at or approximately at the same time, in which when a single image is captured having both eyes of a subject a dimension extends in the single image associated with zero head tilt, and when two images are captured each having a different eye of the subject each of the sensor arrays are calibrated along a common plane to enable locations in images of different eyes of a subject captured by the sensor arrays to be related to coordinates along the common plane, and a dimension along the common plane is associated with zero head tilt; determining a location of a predefined feature associated with each of the different eyes of the subject present in the single image or two images, in which when two images are captured the location of the predefined feature is determined in each of the images in coordinates along the common plane; determining an angle between a virtual line extending between the two eyes of the subject, in which the virtual line extends through the location of the predefined feature of each of the different eyes of the subject in the single image or two images, and the dimension associated with zero head tilt along the single image or the common plane, respectively; segmenting left and right iris images from the single image or two images of the different eyes of the subject; and rotating the segmented left and right iris image in accordance with the angle to substantially remove head tilt when present in the left and right iris images.

In the prior art, a common problem in iris identification (or recognition) systems is the possibility of relative rotation of the iris image between the reference or enrollment image and the presented image. This is accommodated by matching a subject's iris image against a multitude of reference iris images that are effectively rotated at various angles to represent different possible relative rotations between the subject's iris image and each of the reference iris images. The present invention uses information from both eyes in one or two captured images to calculate the angle between the virtual line (e.g., interpupillary line between the pupil centers when such pupils represent the predefined feature) and the sensor array(s) horizontal axis (e.g., a line extending between the right and left sensor arrays or in a single sensor array calibrated to represent the horizontal dimension), allowing correction of the relative rotation between these two lines to produce two canonical images in which the interpupillary line is parallel to the calibrated horizontal axis of the sensor array(s) along the common plane or horizontal axis of a single sensor array. Alternatively, an image of a single eye from a single sensor array may be used to calculate an angle between certain characteristic features of the eye (e.g., the nasal and temporal canthi) and a dimension relating to the head tilt. As a result, the number of possible relative rotations that must be examined is reduced significantly to only one, thereby increasing the match speed by as much as an order of magnitude. In contrast, U.S. Pat. No. 5,291,560, for example, describes the examination of seven different relative orientations between the reference and presented images. Performing matching at seven different relative orientations takes seven times longer than matching at a single relative orientation.

The database having identification data associated with iris images of a plurality of subjects may further contain the IPD or IPD-to-iris ratio for each subject. To accelerate comparative searching, the database may be partitioned in accordance with different values or ranges of IPD or IPD-to-iris ratio, such that the identification data of only the partition having the value or range associated with a determined IPD or IPD-to-iris ratio value is comparatively searched. This is particularly useful for applications wherein the database is large such as >1 million.

The advantage of using the IPD-to-iris ratio is that this ratio does not change with image magnification variations of the optical system for imaging onto sensor array(s). Such magnification variations can be attributed to different distances at which the subject may be positioned relative to the eye capture device as well as to the typical variability in focal length of an objective lens that occurs during manufacturing (typically 1 to 2%). One or more of IPD and IPD-to-iris ratio may be used as additional parameters to iris matching.

By knowing the IPD of an individual, it also becomes more difficult to fake an iris capture system with a fake iris contact lens, since in addition to having very good reproductions of another person's irises printed or painted on a pair of contact lenses, the imposter must also have the same IPD as the subject he is impersonating.

Further, information regarding head tilt may also be used for spoof detection. By determining the absolute orientation of the interpupillary line and hence the absolute position and particularly angular orientation of the iris relative to the interpupillary line, the probability of falsely accepting fake iris contacts as being real drops significantly. Contact lenses are not affixed to the eye and can therefore rotate. For people who do not have astigmatism and who wear contacts for corrective vision purposes, this rotation is not an issue since it does not affect the corrective properties of the contact. However, for the case where a false iris pattern is printed on a contact lens, rotation of the contact lenses can be detected by the apparatus, thereby identifying the false iris. Weights can be attached to one side of a contact lens in order to give the contact lens a preferred axial orientation such as is done for toric contact lenses that are designed to correct astigmatic vision issues. However, the weighting of contacts does not precisely fix the orientation of the contacts since rotations of a few degrees will not affect the vision of the subject wearing said contacts. Rotations of a few degrees may be detected by the apparatus in this manner to detect a false iris.

When the processor segments the left and right iris images from the captured single image or two images of the different eyes of the subject, it first determines boundaries of pupil and iris, and location of the upper and lower eyelids, for each of the different eyes in the single image or two images, in which the segmented left and right iris images represent the portion of the single image or one of the two images between the boundaries of the pupil and iris of the left and right eye, respectively, not occluded by the eyelids, and when the positions of the upper and lower eyelids with respect to the iris in each of the eyes is not substantially the same, the one or two sensor arrays capture another of the single image or two images and at least the segmenting is operative upon such another of the single image or two images. By determining that the location of eyelids is at or near the same with respect to each of the eyes of the subject verifies that the correct eyelid configuration has been detected in both eyes.

Biometric information derived from both left and right eye images can be combined at a number of stages in the identification process. The combination, or fusion, of biometric information can be accomplished at the sample level, in which the right and left eye images are combined; at the feature level, in which the extracted iris images (preferably in polar format) are combined into a single image; at the template level, in which the right and left biometric templates are combined into a single template; or at the decision (or score) level, in which matching is performed separately on the right and left templates and the resulting matching scores are combined to produce a final decision. The combination of scores can be based on several techniques, which by way of example, may include Bayesian decision theory or neural networks.

The present invention offers significant improvements in the state of the art for iris recognition, since it takes advantage of the fact that in nearly all situations images of two eyes provide twice the information content as that contained in a single eye.

Although preferably head tilt angle (or iris rotation) is determined and used to remove head tilt in iris images of two eyes of a subject, an apparatus and method is also described for determining head tilt angle using an image of a single eye, which may then be used to remove head tilt (or iris rotation) in an iris image segmented from such image. Such method may be utilized to improve existing iris identification systems which perform comparative searching over many relative rotations between each template of iris reference images and the template of a presented iris image in a range of expected relative rotation eliminating the need for relative rotations to the one relative rotation in accord with the determined head tilt angle. Alternatively, relative rotation may be eliminated by removing substantially head tilt in this manner in iris images captured at identification, verification, and enrollment of subjects, thus comparative search requires no relative rotation since in both templates iris rotation has been substantially eliminated.

Although in the following the term subject or subjects is referred to a person or people, respectively, iris identification may be of other subjects, such as animals (e.g., horses or dogs).

DETAILED DESCRIPTION OF THE DRAWINGS

The foregoing objects, features and advantages of the invention will become more apparent from a reading of the following description in connection with the accompanying drawings, in which.

Figure 1:
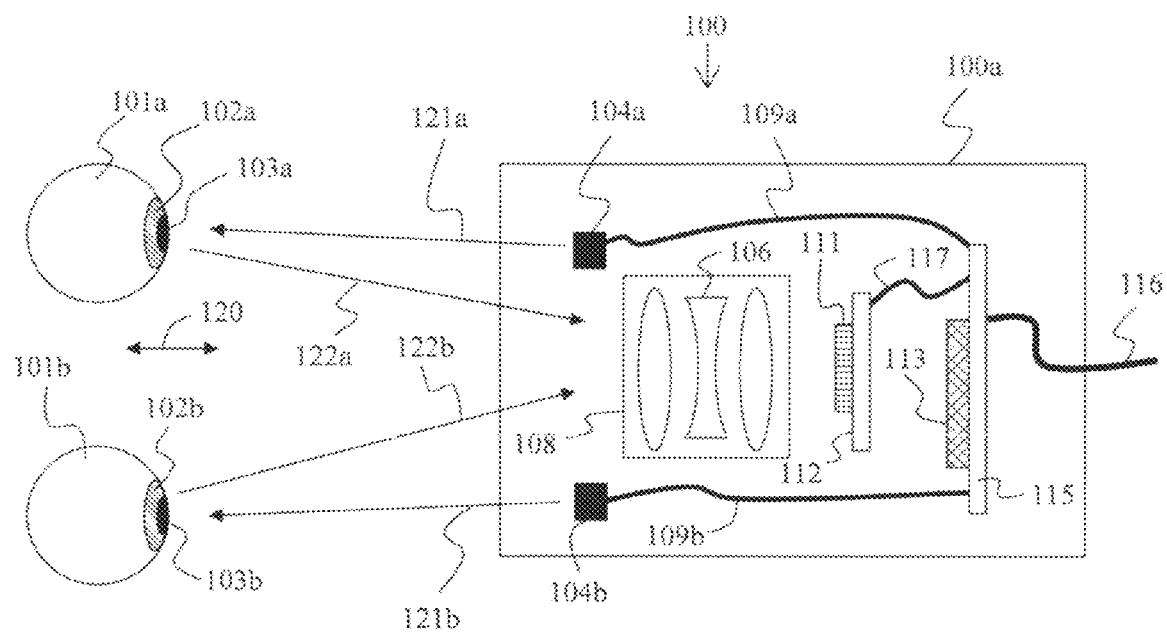
FIG. 1 is a block diagram of an iris capture device in accordance with the present invention to capture both eyes using a single sensor array.
Figure 2:
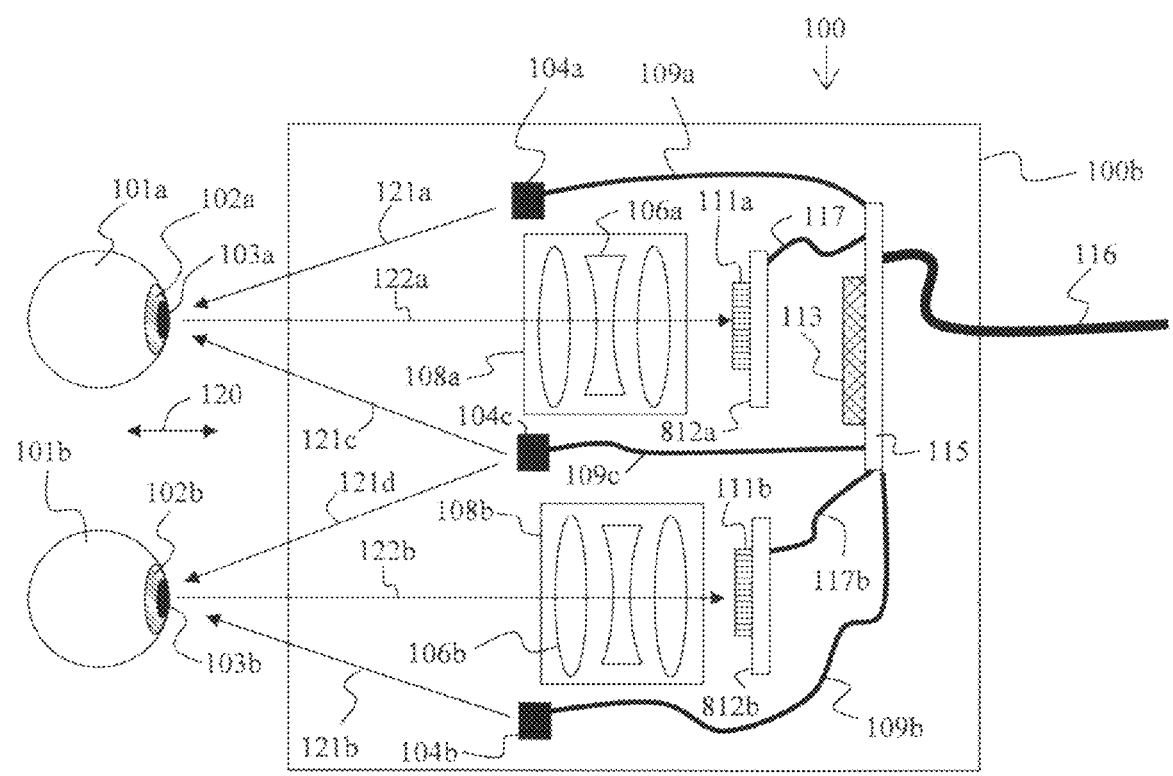
FIG. 2 is a block diagram of an iris capture device in accordance with another embodiment using two sensor arrays which separately capture images of the right and left eyes of a person at, or approximately at, the same time.
Figure 3:
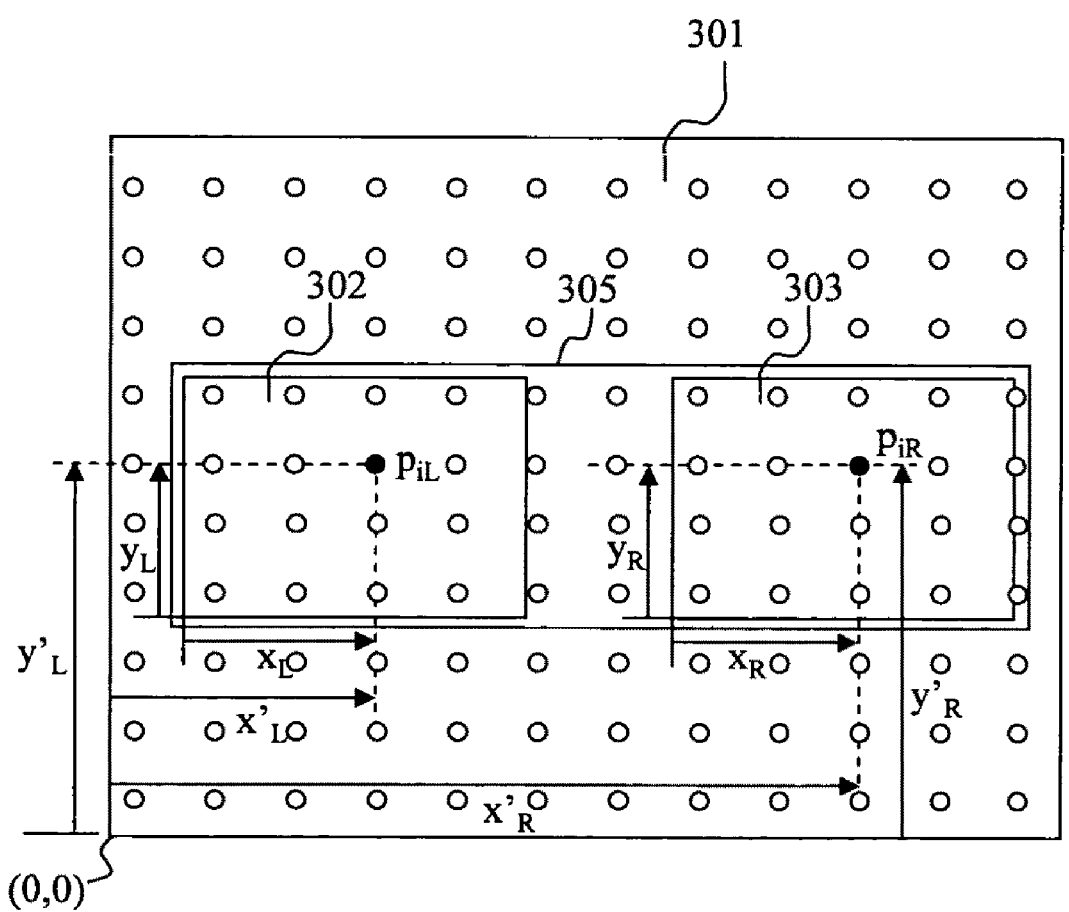
Figure 4:
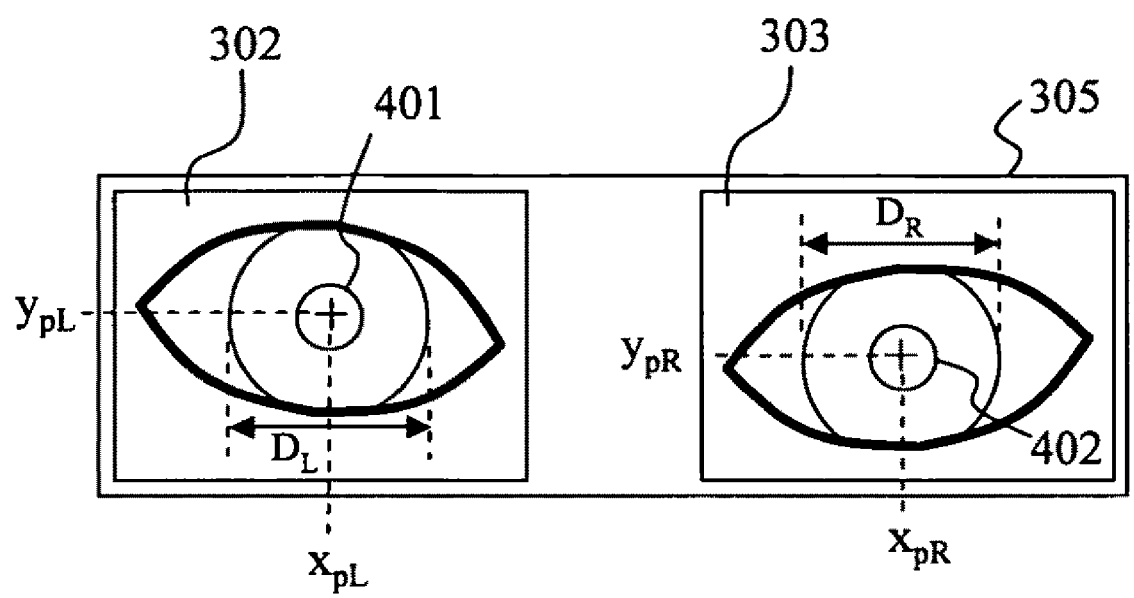
Figure 5A:
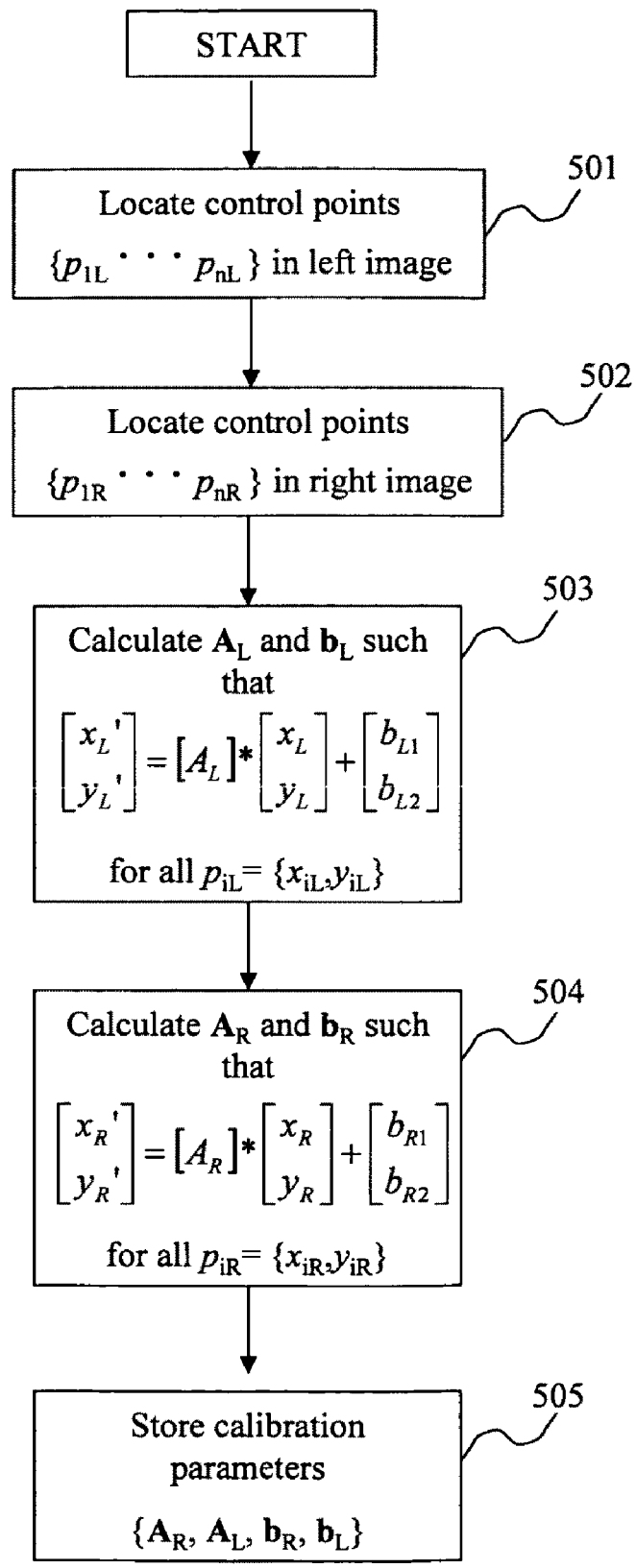
Figure 5B:
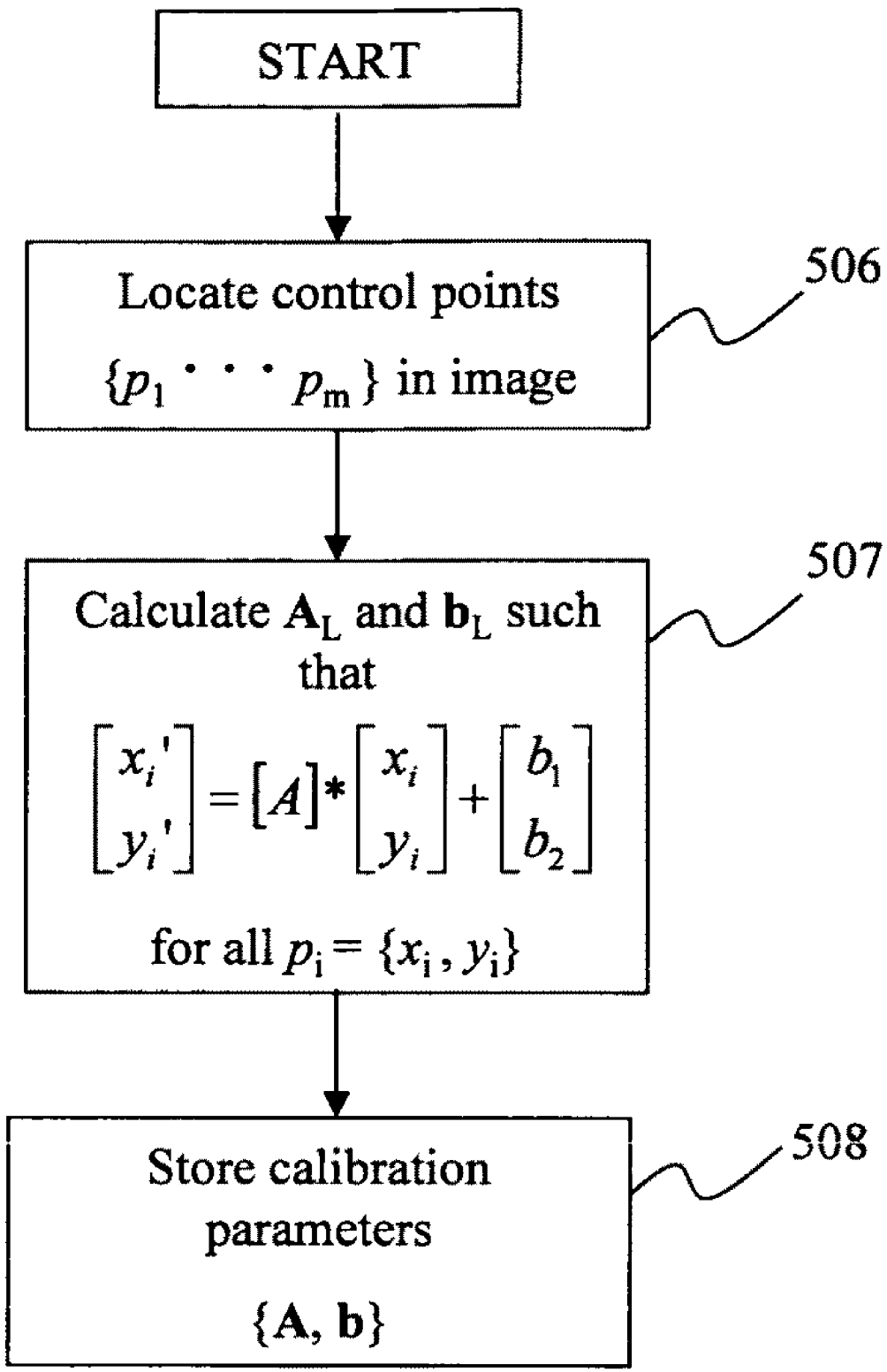
Figure 6:
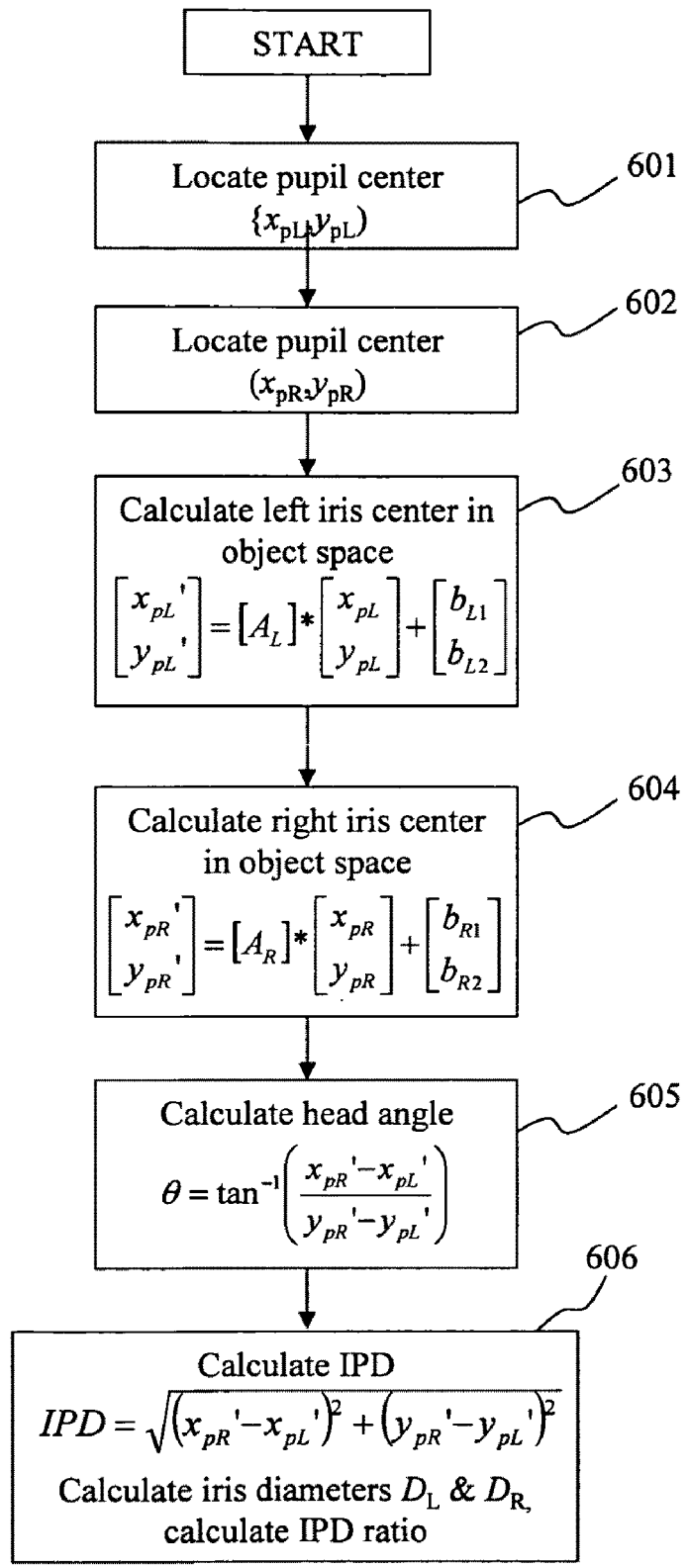
Figure 7A:
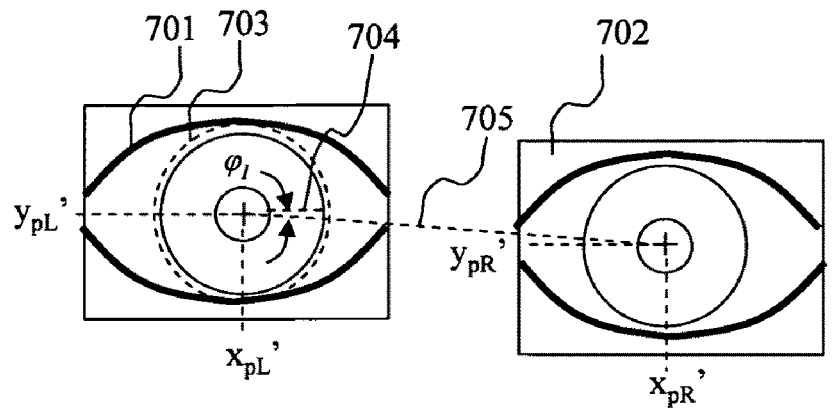
Figure 7B:
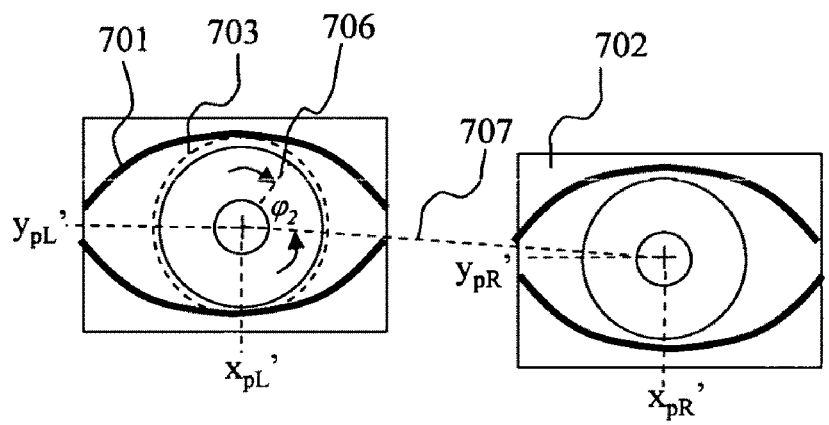
Figure 8:
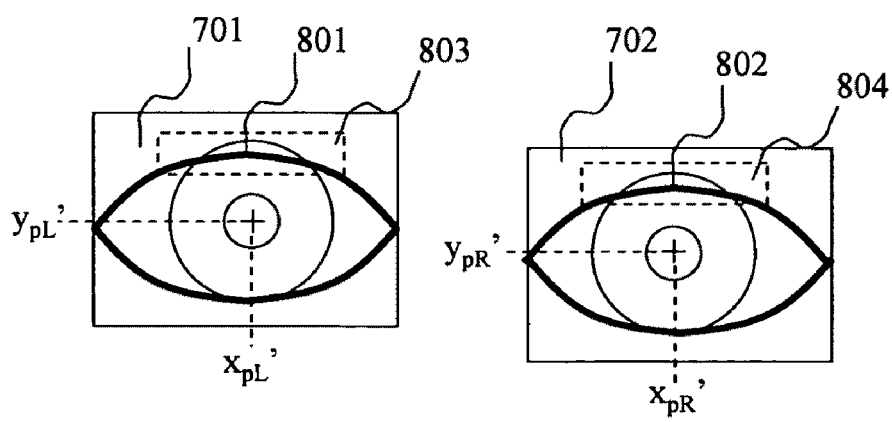
Figure 9A:
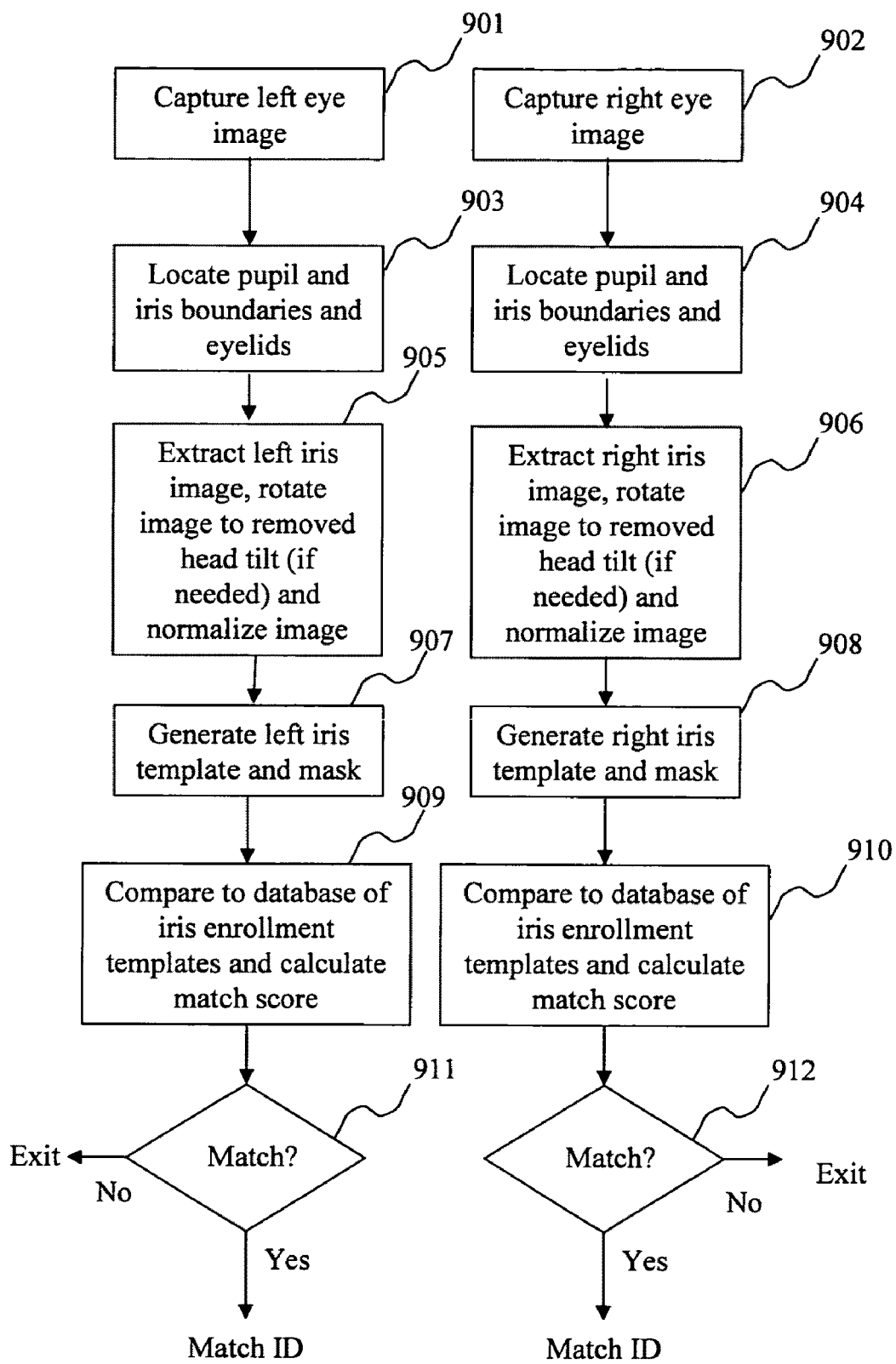
Figure 9B:
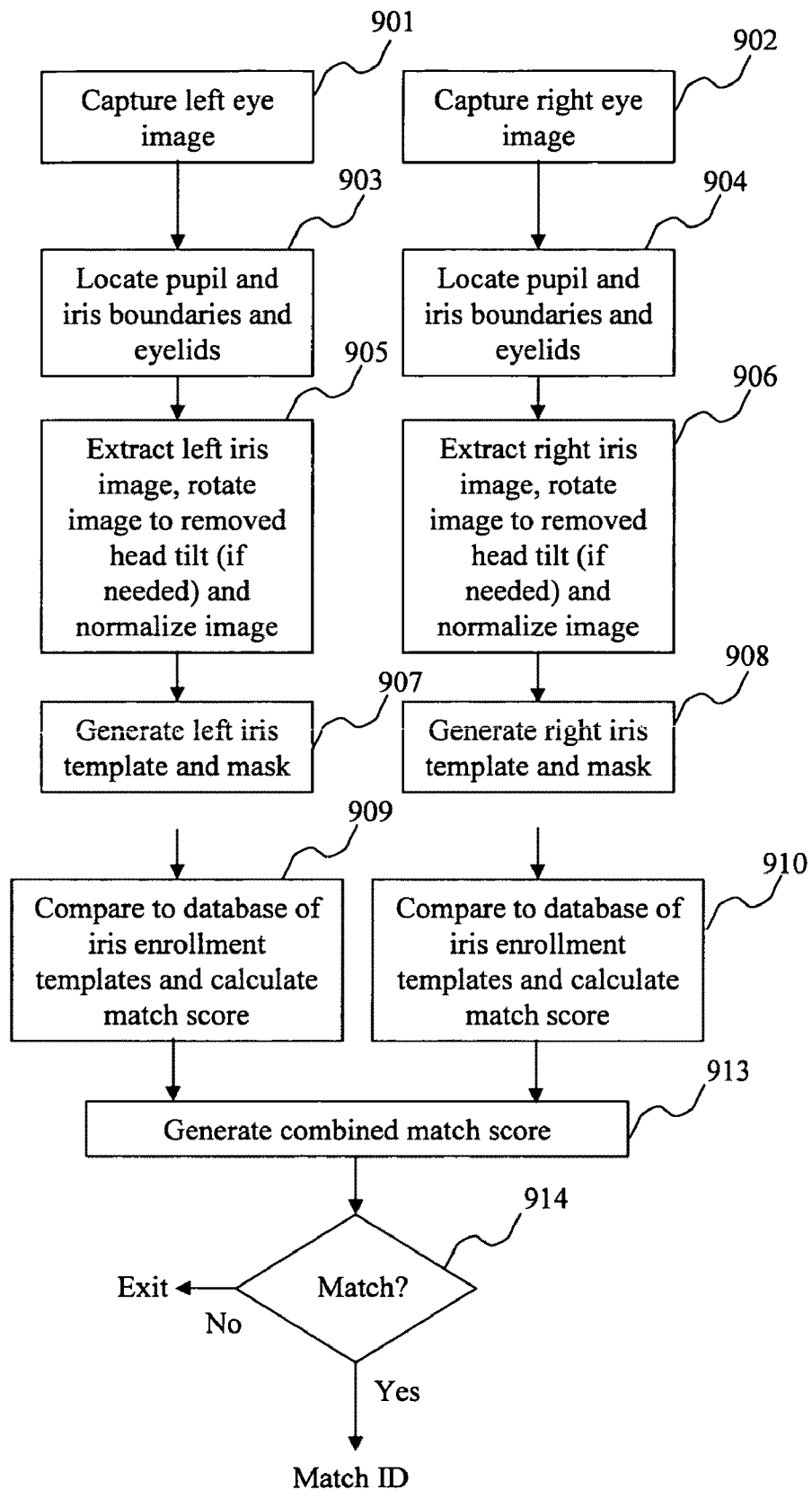
Figure 9C:
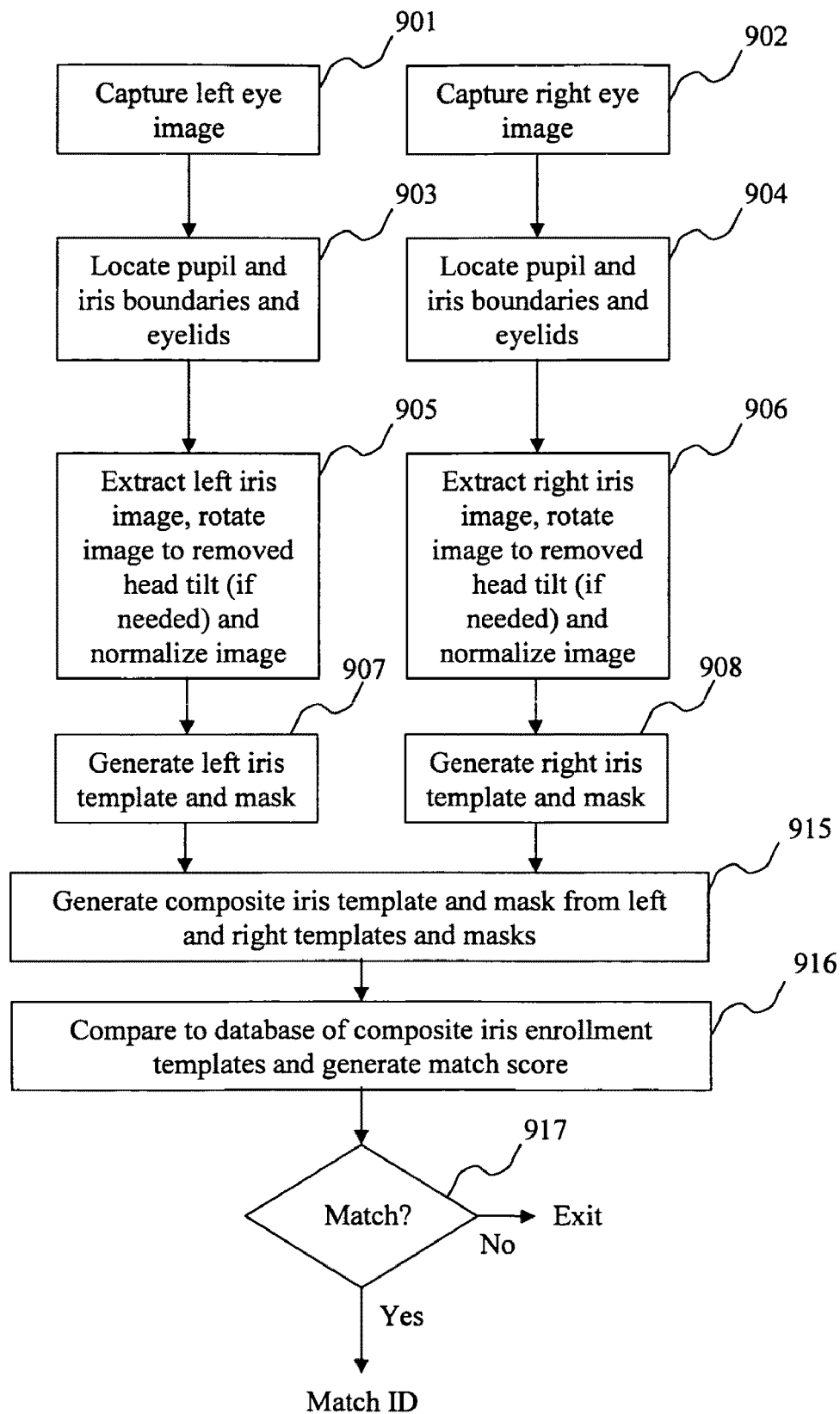
Figure 9D:
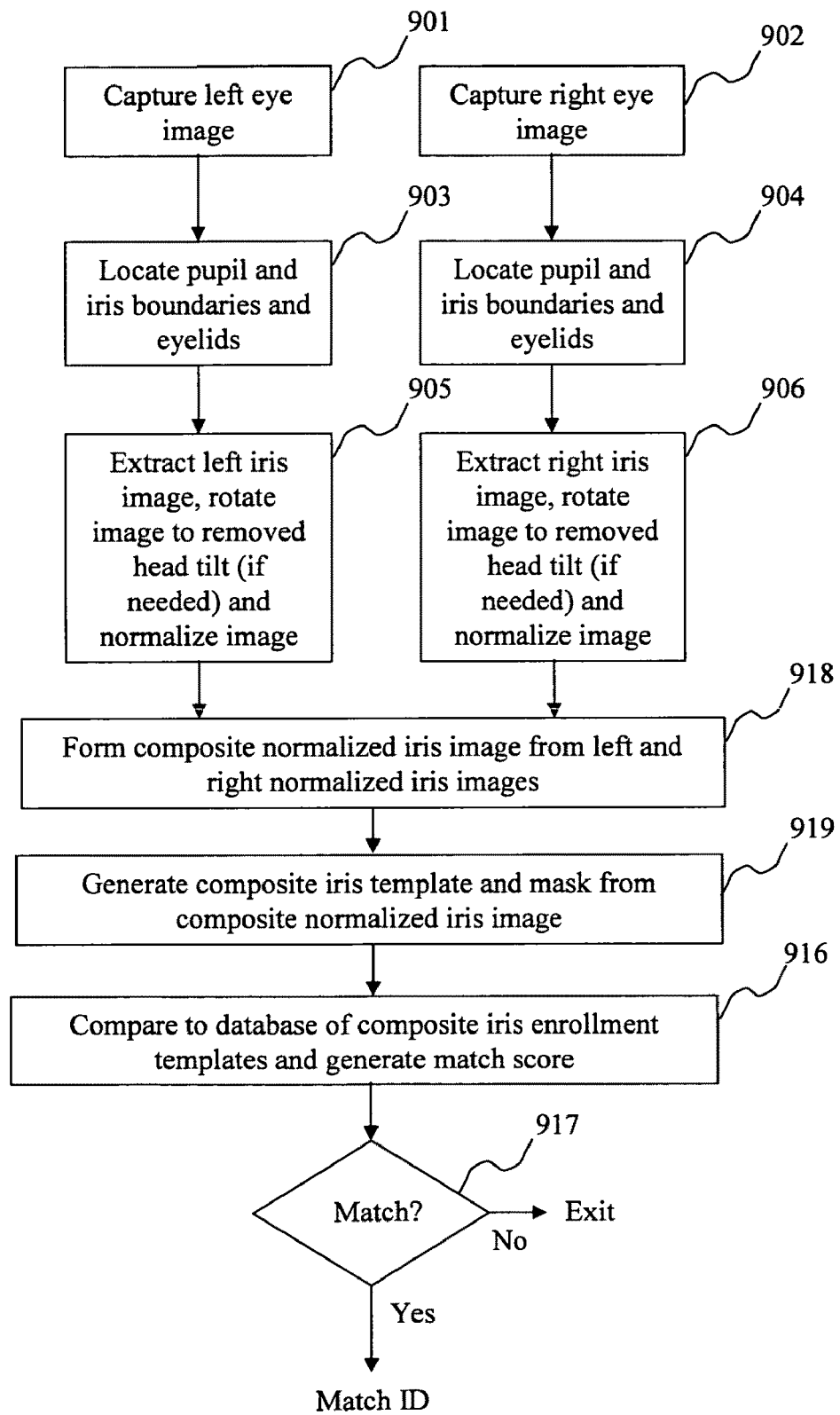
Figure 10:
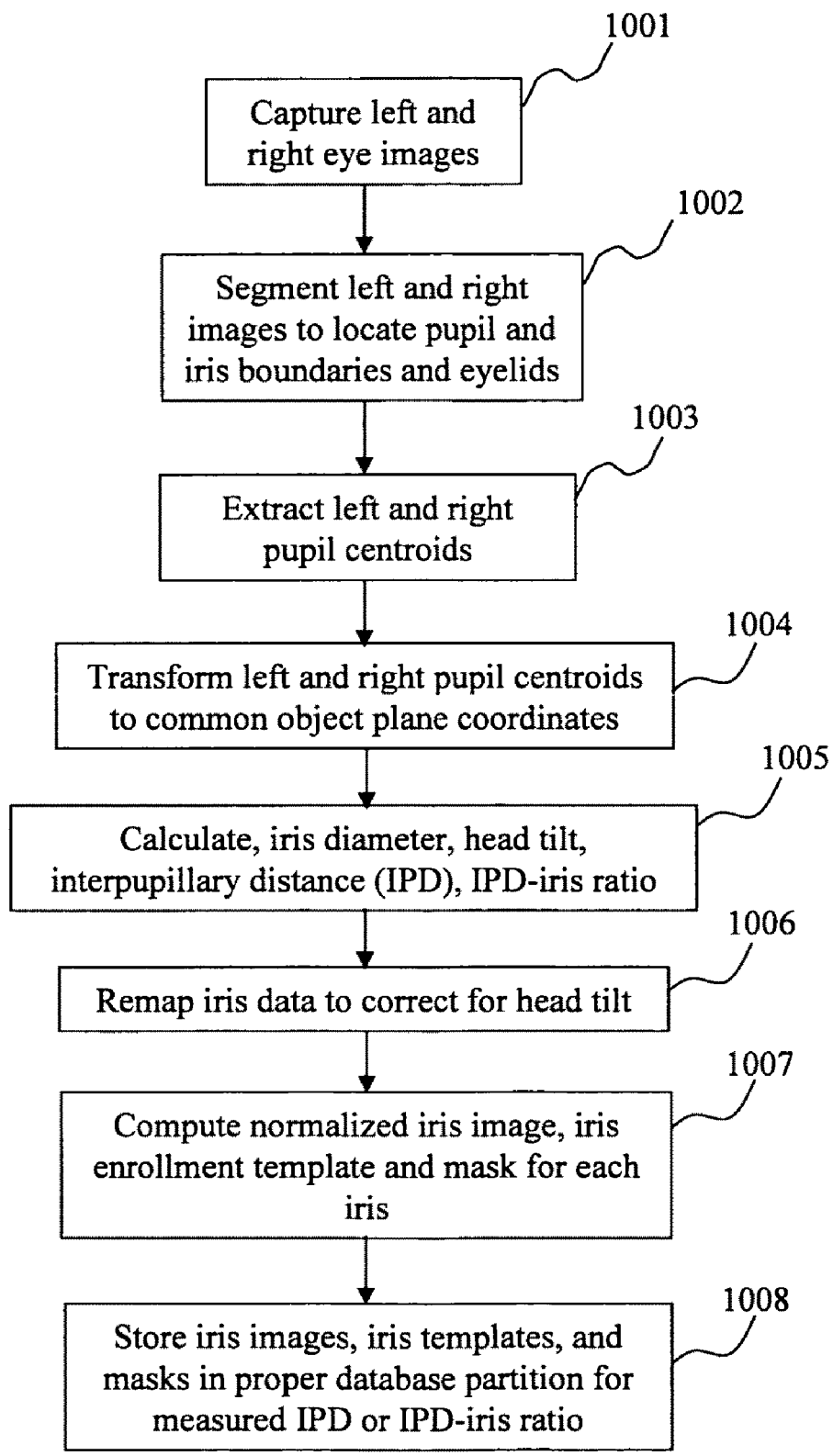
Figure 13:
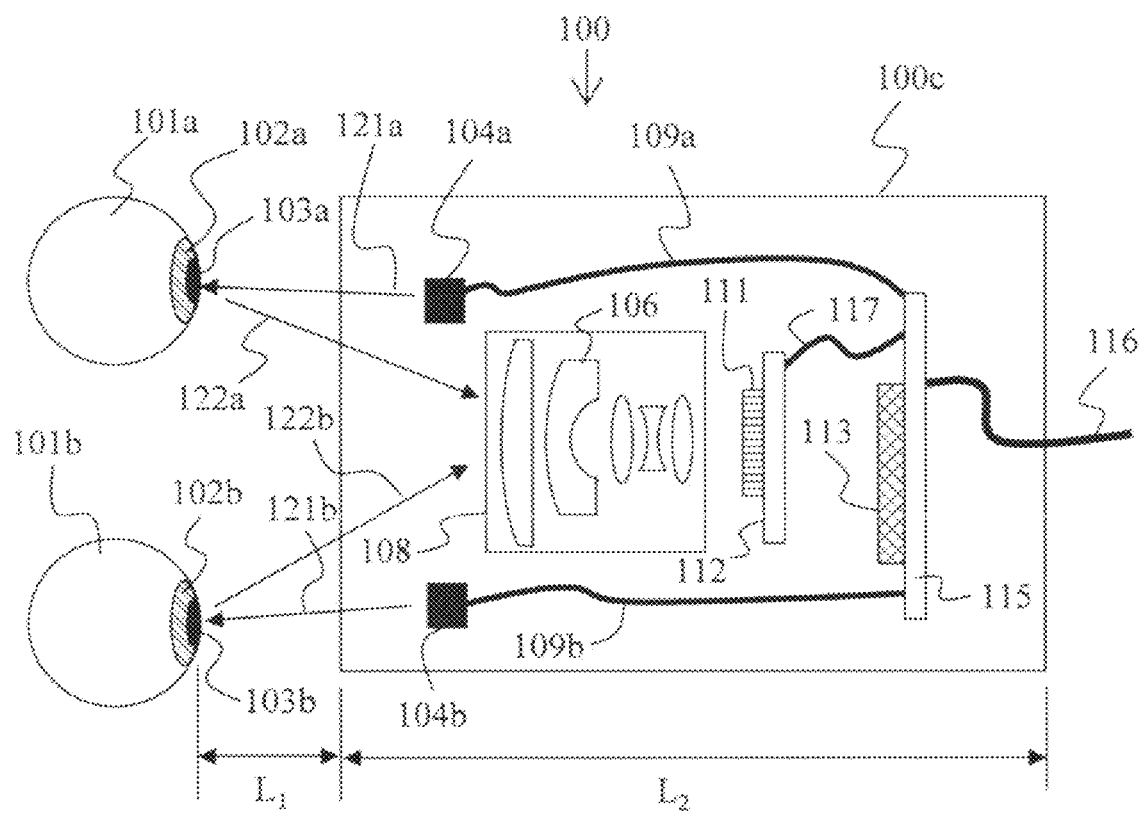

FIG. 3 is an illustration of a calibration target or form which shows the calibration process by which two-dimensional pixel positions of images captured by two sensor arrays of FIG. 2 are calibrated to a single two-dimensional object plane coordinates at a distance where the eyes of a person of FIG. 2 are located with respect to the two sensor arrays, and a single image of both eyes captured by the sensor array of FIG. 1 calibrated to a single two-dimensional object plane coordinates at a distance where the eyes of a person of FIG. 1 are located;

FIG. 4 is an example of right and left eye images captured by each of the sensor arrays of FIG. 2, or a single image of both eyes captured by the sensor of FIG. 1 processed to determine the pupil centers;

FIG. 5A is a diagram of the process of using the calibration form of FIG. 3 to generate transformation (or calibration) data to transform pixel position in images captured by the sensors of FIG. 2 to two-dimensional object plane coordinates;

FIG. 5B is a diagram of the process of using the calibration form of FIG. 3 to generate transformation (or calibration) data to transform pixel position in images captured by the sensor of FIG. 1 to two-dimensional object plane coordinates if calibration of such sensor is performed;

FIG. 6 is a diagram of the process for determining head tilt angle, interpupillary distance (IPD), and IPD-to-iris ratio using images of right and left eye for the iris capture device of FIG. 2, in which IPD determination is optional;

FIGS. 7A and 7B is an illustration of a right and left eye images captured by each of the sensor arrays of the iris capture device of FIG. 2 to show detection of an iris spoof contact lens;

FIG. 8 is an illustration of a right and left eye images captured by each of the sensor arrays of the iris capture device of FIG. 2 to show detection of eyelid position;

FIG. 9A is a flow chart showing the iris recognition processes in an iris identification system using left and right iris images captured by the device of FIG. 2, in which the identification data characterizing each of the irises images are independently determined and compared to a database of identification data to arrive at an independent match scores for each iris image;

FIG. 9B is a flow chart showing the iris recognition processes in an iris identification system using left and right iris images captured by the device of FIG. 2, in which identification data characterizing each of the iris images are independently determined and compared to a database of identification data to arrive at a combined match scores with respect to both irises;

FIG. 9C is a flow chart showing the iris recognition processes in an iris identification system using left and right iris images captured by the device of FIG. 2, in which identification data characterizing each of the irises images are combined and compared to a database of identification data to arrive at match scores with respect to both irises;

FIG. 9D is a flow chart showing the iris recognition processes in an iris identification system using left and right iris images captured by the device of FIG. 2, in which identification data is generated from a composite of both iris images and compared to a database of identification data to arrive at a combined match scores;

FIG. 10 is a flow chart of the enrollment process in accordance with the present invention;

FIG. 11A is an illustration of an example eye to show normalization of an iris image into polar coordinates;

FIG. 11B is an illustration of the iris image of FIG. 11A after normalization into polar coordinates;

FIG. 12 is an example of a left eye image illustrating the use of a virtual line between the eye corners to correct for head tilt in an iris image; and FIG. 13 is a block diagram of an iris capture device similar to the iris capture device of FIG. 1 using an optical system having wide angle lens(es) for imaging onto a sensor array.

DETAILED DESCRIPTION OF THE INVENTION

Referring to FIGS. 1 and 2, an iris capture device (or apparatus) 100 is shown having in one embodiment a housing 100a with a sensor array 111 (FIG. 1) for capturing both eyes 101a and 101b of a subject person in a single image, and in another embodiment a housing 100b having two sensor arrays 111a and 111b (FIG. 2) each for capturing a different eye 101a and 101b, respectively, of a subject person.

In FIG. 1, the housing 100a further has an optical system 108 composed of one or more optical elements or lenses 106 which focuses and relays light representing a two-dimensional (2-D) image of the two irises 102a and 102b onto sensor 111. Sensor 111 may comprise a 2-D array of sensor elements, such as a complementary metal-oxide semiconductor (CMOS) or a charge-coupled device (CCD), or a one-dimensional (1-D) sensor array mechanically scanned to generate a 2-D image. The focus adjustment may be set by the operator or subject by physically moving the device 100 bi-directionally along the arrow 120 (or by the subject moving towards or away from the device 100 along the direction given by arrow 120) and thereby changing the iris-to-optical system distance. Alternatively the iris capture device 100 can incorporate an autofocus and/or range finding device in order to set the correct object distance and achieve optimal focus settings. Preferably the field-of-view of optical system 108 encompasses a maximum IPD of at least 72 mm (e.g., 95th percentile for adult humans) and sufficient area outside this IPD to capture up to a 13.5 mm diameter iris and allow for a level of lateral displacement error. Additionally, the optical and electronic resolution of imaging onto sensor 111 should be sufficient for the level of precision needed for iris matching, which may meet or exceed certain standardized iris image capture specifications, such as for example, Iris Image Interchange Format ANSI INCITS 379-2004. Using this specification and choosing Medium Image Quality, the device's camera (defined as the combination of optical system 108 and sensor 111) requires >12.5 pixels/mm electronic resolution, 60% MTF for 3 cycles/mm at the iris, and at minimum a border of 70 pixels captured outside of the iris. For example, for 15 pixels/mm the sensor 111 may be a 5 megapixel monochrome CMOS model MT9P031M available from Aptima Imaging (San Jose, Calif.), which has an array of 2592×1944 pixels and allows for a lateral displacement error of ±39 mm and ±53 mm in the horizontal and vertical axes, respectively. The larger the allowed lateral displacement error the better as this allows for less precise alignment of the subject person to the iris capture device and hence faster iris captures.

Sensor 111 is mounted to a printed circuit (PC) board 112 that is connected via power/communication cable 117 to control board 115. Control board 115 is preferably connected to one or more light sources 104a and 104b, via power cables 109a and 109b. For purposes of illustration two light sources are shown, but other number of light sources may be used. Such light sources preferably project visible and near infrared light at the irises of the subject and may contain lenses if needed for increasing the efficiency with which light illuminates the subject's irises. Light from the light sources 104a and 104b is projected towards the irises 102a and 102b (rays 121a and 121b, for illustration) and the light scatter from the iris, for example rays 122a and 122b are imaged by optical system 108 onto sensor 111. Visible light of suitable intensity is preferential to constrict the pupil of the subject for liveness detection and for maximizing the iris area observed. Near infrared light, for example 760 and 850 nm wavelength is preferable for recording the image of the eye as these wavelengths have been found to produce superior iris detail. Sensor 111 provides an image of both eyes 101a and 101b, that includes at least both irises 102a and 102b and pupil 103a and 103b, to the one or more processors 113 on a control board 115 in housing 100a. Sensor 111 may have a control processor and a local image buffer for temporary image storage and image processing (e.g., distortion correction and/or flat-field correction) of a two-dimensional array of bytes representing the image prior to such transfer.

In the FIG. 2 embodiment, the iris capture device 100 is provided by housing 100b having two optical systems 108a and 108b each having one or more optical elements or lenses 106a and 106b, respectively, for focusing and relaying light of only one eye 101a and 101b, respectively, onto sensor arrays 111a and 111b, respectively. One or more illumination sources 104a, 104b, and 104c in housing 100b may be the same as the one or more illumination sources in the FIG. 1 embodiment. One advantage of having two optical systems 108a and 108b is that sensors 111a and 111b, which may each be of the same type as sensor 111, do not have to be as large as that of the single sensor 111, and are therefore generally less expensive and capable of higher frame rates. For example, each of sensors 111a and 111b may be capable of capturing an image at 15 pixels/mm using an SXGA CMOS (1280×1024 pixels). For example, with a maximum iris diameter of 13.5 mm and an iris edge to image border requirement of 70 pixels per ANSI INCITS 379-2004, there can be lateral displacement errors of ±31 mm and ±22.5 mm in horizontal and vertical directions, respectively. Each of the sensors 111a and 111b provides an image of their respective iris 102a and 102b and pupil 103a and 103b to the one or more processors 113.

Processors 113 in FIGS. 1 and 2 may have memory for storing received image(s) from sensor 111, or sensors 111a and 111b, or such memory may be provided on control board 115 and accessible to processors 113. The processors 113 may represent electronics similar to a digital camera for capturing images from a CCD or CMOS sensor, such as a microprocessor or microcontroller programmed in accordance with software, or processors 113 may represent one or more field-programmable gate arrays (FPGA).

Preferably, processors 113 segment left and right iris images for the captured image from the sensor 111, or sensors 111a and 111b, respectively, and send such segmented images to a computing system, via cable 116 or alternatively via a wireless transmitter, where such images are processed to provide left and right iris images having zero or substantially zero head tilt, which are then normalized into rectangular images having polar radial coordinates, and converted into left and right iris templates for iris matching for identification or verification of a subject, or for enrollment of a subject with respect to a database of identification data in an iris identification system. Such image processing to remove head tilt, normalization, and template generation may all be performed by processors 113 in housing 100a or 100b. Furthermore, iris matching (for identification or verification) or enrollment may also be performed in housing 100a and 100b where the processor 113 having access to memory in the device 100 storing a database of identification data, or where such database may be externally available via an interface of the device. In a further alternative, the processing to remove head tilt, normalization, and template generation, and iris matching (for identification or verification) or enrollment, may be performed in a computer system in response to images received from sensor(s) from housing 100a or 100b.

Figure 2A:
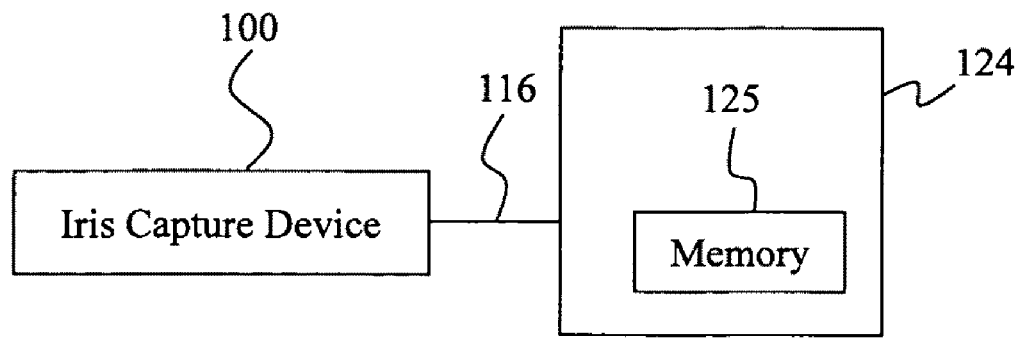
FIG. 2A is a block diagram of an iris identification system in accordance with the present invention having an iris capture device of FIG. 1 or 2 and a computer system having a database of identification data for use in comparative iris(s) matching.

An example of iris image capture device 100 connected to a microprocessor-based system, such as a computer system 124, is shown in FIG. 2A. For purpose of illustration the database 125 is shown in memory (e.g., optical or hard drive, or a flash drive) of computer system 124 for enrollment to add identification data (e.g., left and right iris templates along with subject's name and other personal information), or comparative matching to identification data (e.g., stored left and right iris templates of others) to identify (or verify) the subject with respect to acquired iris images by device 100. Image processing, normalization, template generation, matching and enrollment provided by processors 113 in device 100 or by a combination of processors in device 100 and those present in computer system 124, will be described later in more detail.

Power to components in housings 100a or 100b may be provided via the cable 116 from computer system 124, or rechargeable battery within housings 100a or 100b, or power supplied externally via an AC power adapter. The computer system 124 and device 100 also have interface hardware/software to enable data communication between them, and if needed to control the operation of sensor(s) 111 or 111a and 111b, processor(s) 113, and light sources 104a, 104b, or 104c to capture image(s). Computer system 124 includes a user interface (e.g., display, keyboard, mouse, or the like) to enable a user to interact with the software operating iris identification system in memory of the computer system 124 and/or iris capture device 100, as typical of an iris identification (or recognition) system to output match results, to indicate verification of identity with respect to inputted subject information to the computer system, or to confirm enrollment, but capable of using both left and right iris images (or being operable in a mode using a single eye image as described later in connection with FIG. 12). However, other user interfaces may be used, such as green and red colored LEDs on housing 100a or 100b, or computer system 124, to determine if good image(s) were captured, or if a match was found in the database.

The magnification and distortion errors of the iris capture device 100 can be calibrated using a target (or calibration) form, such as printed media, placed at the nominal iris positions, i.e., at the distance the irises 102a and 102b of a subject would be located with respect to the sensor 111, or 111a and 111b, and their respective optical systems. Such target may contain, by way of example, a series of horizontal and vertical lines as well as a series of circles for the accurate calculation of centroid locations for determining distortion errors that may affect the accurate extraction of iris images and calculation of head tilt angle (and IPD or IPD-to-iris ratio if determined) as will be described later in more detail. Both embodiments of FIGS. 1 and 2 are calibrated in the same way; however, relative lateral positions and rotations of optical systems 108a and 108b may need to be calibrated first mechanically to enable accurate calculation of head tilt angles and IPD prior to electronic calibration of sensors using the target form. Further discussion of the electronic calibration is provided below in connection with FIGS. 3, 4, 5A, and 5B.

For purposes of the following discussion, each optical system 108a and 108b and sensors 111a and 111b, respectively, are referred to as left and right cameras, respectively. The left and right cameras are preferably positioned on the same horizontal plane but separated by a distance approximately equal to the average interpupillary distance (IPD), which is about 62 mm in adult humans. Each camera may have its own infrared illumination 104a and 104b, consisting, by way of an example, of an array of one or more illumination sources, which may be light-emitting diodes, positioned adjacent to the camera optics 108a and 108b. Each camera may have a fixation device or light 104c, which may also be used for iris illumination that is activated when the images are captured to assure consistent gaze angle relative to the camera axis. Each camera's sensor 111a and 111b may have a control processor and a local image buffer to assure precise simultaneous or nearly-simultaneous capture by both sensors.

For the dual sensor iris capture device 100 of FIG. 2, FIG. 3 illustrates the images 302 and 303 produced by the left and right cameras, respectively, superimposed on the object-space calibration target 301. The target or calibration form contains an array of control points [$p_1, p_2, \ldots p_n$], two of which are shown as points $p_{iL}$ and $p_{iR}$. Each such control point is recorded on the calibration target as a circular area with diameter equal to approximately 10 times the object plane pixel size of the camera. By way of example, if the camera pixel size is 0.005 mm each control point would be printed on the calibration target as a circle having a diameter of approximately 0.5 mm (equal to 10·M·0.005 mm where M is the magnification of optical system 108a and 108b). Thus in the image produced by the camera, each control point will have a diameter of about 10 pixels. The centroid of each such circular object constitutes the precise location of the control point and can be determined with subpixel precision. By way of example, to determine a centroid position in an image for each of the control point, a binarization of the gray scale values (or intensity) of pixels of an image is performed to generate a binary map to locate pixels associated with the control point's boundary (or circular object), and using a percentage of pixels (e.g., 20%) beyond or outside such boundary to determine a binary region R. A series of geometric moments is then computed for each circular object such that the moment $m_{pq}$ for the binary region R associated with that object in the map is defined as $$m_{pq} = \sum_R x^p y^q$$

The summation is performed over all pixel locations (x,y) within the interior of a single circular object. The centroid ($x_c$, $y_c$) of said circular object is then given by:

$$x_c = m_{10}/m_{00}$$

$$y_c = m_{01}/m_{00}$$

such as described in O'Gorman, L., Sammon, M., and Seul, M., *Practical Algorithms for Image Analysis*, (Cambridge University Press, New York, N.Y.) pp. 157-159, 2008.

The locations of the control points are defined by coordinates (x', y') within a two dimensional coordinate system defined by the calibration target 301. In FIG. 3 the control point $p_{iL}$ is located at pixel location ($x_L, y_L$) within the left image. Similarly, the control point $p_{iR}$ is located at pixel location ($x_R, y_R$) within the right image. It is understood that points $p_{iL}$ and $p_{iR}$ are representative of control points within the calibration target, and each camera image contains at least three such control points. By way of example, within the coordinate system defined by the calibration target, control points $p_{iL}$ and $p_{iR}$ are located at coordinates ($x_L', y_L'$) and ($x_R', y_R'$), respectively. The purpose of the calibration process is to define a mathematical transformation that defines the relationship between points such as ($x_L, y_L$) and ($x_R, y_R$) in the left and right images and the corresponding points ($x_L', y_L'$) and ($x_R', y_R'$) in the object space (or coordinate system) defined by the calibration target. A separate calibration is performed for each of the left and right camera which simultaneous (or approximately simultaneous) capture images of the same calibration target presented before the cameras, and the resulting transformations consist of transformation data representing a rotation and scaling matrix and a translation vector for each camera in which one or more two-dimensional pixel coordinates in an image captured either sensor 111a or 111b is transformed into two dimensional object coordinates with respect to features or objects in the image. These transformations are described later in connection with FIG. 5A. Although only three points are needed to determine each transformation, additional points may be required to correct for optical distortion due to each camera's optical systems 108a or 108b.

The above calibration for the dual sensor iris capture device 100 of FIG. 2 is not needed in the single sensor iris capture device 100 of FIG. 1. However, calibration of images captured on sensor 111 may be performed when an actual measure of IPD, referred to herein as an absolute IPD, is needed, or when optical distortion is present in an image captured by the sensor 111 which if uncorrected will produce a larger than acceptable head tilt angle calculation (or IPD-to-iris ratio, if calculated). Such optical distortion can occur due to the particular lens(es) of optical system 108. Such calibration if needed is similar to that described above in connection with FIG. 2, but with respect to a single image 305 captured having both right and left eyes to provide a mathematical transformation that defines the relationship between points such as $(x_L, y_L)$ and $(x_R, y_R)$ in the image and the corresponding points $(x_L', y_L')$ and $(x_R', y_R')$ in the object space defined by the calibration target. This calibration also results in transformation data representing a rotation and scaling matrix and a translation vector in which one or more two-dimensional pixel coordinates in an image captured by sensor 111 can be transformed into two dimensional object coordinates with respect to features or objects in the image.

FIG. 4 illustrates images 302 and 303 of the right and left eyes of a human subject captured by the left sensor 111b and the right sensor 111a in the FIG. 2 embodiment, and image 305 captured by sensor 111 in the FIG. 1 embodiment. The left and right pupil boundaries 401 and 402, respectively, are extracted using typical image segmentation techniques such as integrodifferential operators as described in U.S. Pat. No. 5,291,560 or Hough transforms, as described in earlier cited O'Gorman et al., page 182, and the geometric centers $(x_{pL}, y_{pL})$ and $(x_{pR}, y_{pR})$ for the left and right pupils, respectively, are determined. These geometric centers can be used to determine the orientation and length of a virtual line connecting the geometric centers, but their coordinates must first be transformed to the object space defined by the transformation data for the particular device 100.

Referring to FIG. 5A, a flow chart is depicted for the calibration process using the calibration target 301 described earlier in connection with FIG. 3 for the embodiment of the image capture device 100 of FIG. 2. At step 501 the control points visible in the left image 302 are located and the image space coordinates of at least three control points appearing in the left image are recorded. At step 502, similarly, the coordinates of at least three control points appearing in the right image 303 are recorded. At step 503 a rotation-and-scaling matrix $A_L$ and a translation vector $b_L$ are calculated that together transform the measured image plane coordinates of control points such as $(x_{iL}, y_{iL})$ to the known object plane coordinates $(x_{iL}', y_{iL}')$ for those same points. The object plane coordinates of the control points are known because their positions are labeled on the calibration target. A similar rotation-and-scaling matrix $A_R$ and a translation vector $b_R$ are calculated at step 504 for the right image. The rotation-and-scaling matrix $A_R$ and translation vector $b_R$ for each camera are calculated as an affine transformation, such as described in Foley, J., van Dam, A., Feiner, S., and Hughes, J., *Computer Graphics Principles and Applications*, (Addison-Wesley, Reading Mass.) pp. 204-208, 1990, that is used to transform the image coordinates of points in each image to the common object space coordinate system defined by the calibration target. Such affine transformations define the rotation, translation, and magnification of the two-dimensional image coordinates relative to the two-dimensional coordinate system defined by the target. The calibration parameters represent transformation data which is stored in the memory, such as on board 113 in housing 100a or 100b, or in computer system 124, for use by the processor(s) providing head tilt correction in accordance with captured image(s) in housing 100b, or computer system 124 (step 505).

As stated earlier, the single sensor iris capture device 100 of FIG. 1 may optionally be calibrated. If so, a calibration process using the calibration target 301 described earlier in connection with FIG. 3 for embodiment of device 100 of FIG. 1 is performed as shown in the flow chart of FIG. 5B. At step 506 the control points visible in the image 305 are located and the image space coordinates of at least three control points appearing in the image are recorded. Such control points are represented as circles having known positions within the target 301. At step 507 a rotation-and-scaling matrix A and a translation vector b are calculated that together transform the measured image plane coordinates of control points such as $(x_i, y_i)$ to the known object plane coordinates $(x_i', y_i')$ for those same points. The object plane coordinates of the control points are known because their positions are labeled on the calibration target. The rotation-and-scaling matrix and translation vector are calculated as an affine transformation, that is used to transform the image coordinates of points in each image to the common object space coordinate system defined by the calibration target. The calibration parameters provide transformation data which is stored in the memory in housing 100a, or computer system 124, for use by the processor(s) providing head tilt correction in accordance with captured image(s) in housing 100a, or computer system 124 (step 508).

In both FIGS. 5A and 5B, the processor at steps 501, 502, and 506 compares each value of pixels in the image with a threshold to identify the one or more pixels (or centroid) as being one associated with one of the control point circles in image. Since the control points are in a known series or pattern, the pixel position(s) are matched to each control point that has a particular known two dimensional position associated with the control point stored in memory of the processor or accessible to the processor. Alternatively, coefficients associated with the mapping transform equation (for example the scaling matrix A and translation vector b previously described) for transforming image control point locations to target control point locations are stored in memory accessible to the processor. Although circles are shown as control points other control points, arrangement, or graphical references may be used. Less preferably, the transformation data stored at steps 505 or 508 may represent a look-up-table in memory of the processor(s) 113 or accessible to the processor 113 or computer system 124, that requires use of transformation data, to map pixel positions in an image to object positions in two dimension space. The calibration process of FIGS. 5A and 5B occurs during manufacture, but may also occur later to assure that the transformation data is proper. As stated earlier, the time lag between the capture of images from each of the two sensors 111a and 111b of FIG. 2 should be short compared to the time required to rotate ones head, shift ones eyes, or tilt/rotate the capture device itself. The time lag between the capture of each image by sensors 111a and 111b will dictate the accuracy with which one can determine the orientation of the interpupillary line (imaginary line connecting the centroid of the two pupils). As such, it is preferable that the time lag is near zero and preferably a fraction of a second. In the single sensor iris capture device 100 of FIG. 1, the sensor 111 has sufficient pixel resolution and field of view to assure that both eye images can be captured in a single image frame. As stated earlier, camera orientation/position calibration described above is optional for the single sensor iris capture device 100 of FIG. 1, as all of the information regarding the orientation of the interpupillary line is contained within a single image that contains the two pupils of a single subject's face.

FIG. 6 shows a flowchart for determining the subject head angle and absolute IPD where calibration has been performed to enable transformation of pixel position on sensor(s) and object space coordinates. At step 601, the pixel coordinates of the pupil center in the left eye ($x_{pL}$, $y_{pL}$) are determined as described above in FIG. 4. At step 602 the pixel coordinates for the pupil center for the right eye ($x_{pR}$, $y_{pR}$) are similarly determined. Steps 601 and 602 either utilize the single image of both eyes in the single sensor iris capture device 100 of FIG. 1, or each of the left and right eye images in the dual iris capture device of FIG. 2. At step 603 the left pupil center pixel coordinates are transformed, using the transformation data to object space coordinates. The exemplary equations shown in FIG. 6 for steps 603 and 604 are for the separate left and right eye images and use transformation data $A_R$, $A_L$, $b_R$, and $b_L$ stored at step 505. For a single image with both eyes, the same equations of steps 603 and 604 are used, but with $A_R$ and $A_L$ both equal to A, and $b_R$ and $b_L$ both equal to b, where A and b were stored at step 508 (FIG. 5B). Such storage may be memory in housing 100a or 100b for use by processors 113, and/or memory in computer system 124. The left and right pupil centers in object space are denoted as ($x_{pL}'$, $y_{pL}'$) and ($x_{pR}'$, $y_{pR}'$), respectively, and are defined in the same object space coordinate system. The head angle θ, calculated at step 605, is the angle that the line between the left and right pupil centers ($x_{pL}'$, $y_{pL}'$) and ($x_{pR}'$, $y_{pR}'$) and the horizontal axis of the object space coordinate system, as shown by the following equation:

$$\theta = \tan^{-1}\left(\frac{x_{pR}' - x_{pL}'}{y_{pR}' - y_{pL}'}\right)$$

For example, such horizontal axis being the horizontal line centered vertically in target 301, e.g., passing through $p_{iL}$ and $p_{iR}$ (FIG. 3), representing the absolute zero tilt dimension in device 100.

The interpupillary distance, or IPD, is then calculated at step 606 as the distance between the pupil centers, using the following equation:

$$\text{IPD} = \sqrt{(x'_{pR} - x'_{pL})^2 + (y'_{pR} - y'_{pL})^2}$$

Alternatively, the iris centers may be used instead of the pupil centers to determine head angle and distance between the eyes, since pupil center may change slightly as the pupil dilates and contracts. The iris center is not affected by pupil size but may be more difficult to detect reliably due to obscuration of part of the iris boundary by the upper and/or lower eyelids. In either case the same steps are used to calculate the iris centers. Ocular landmarks other than pupil or iris centers (or centroids) may be used as predefined features for determining the head tilt angle, such as centroids associated with the inner or outer corners of one or both eyes (i.e., nasal canthi and/or temporal canthi). An example of the use of corners in a single eye image to determine head angle will be described later in connection with FIG. 12. If IPD is not utilized as a parameter to facilitate identification, step 606 is not performed.

Head angle and absolute IPD are determinable as described in FIG. 6 using the resulting positions in object coordinate system of pixel position of the pupil or iris centroid. If no calibration is performed as may be the case for the single sensor iris capture device 100 of FIG. 1, then steps 601 and 602 are performed to locate pupil center ($x_{pL}$, $y_{pL}$) and ($x_{pR}$, $y_{pR}$), and head angle is determined by substituting $x_{pL}$, $y_{pL}$, $x_{pR}$, $y_{pR}$ for $x_{pL}'$, $y_{pL}'$, $x_{pR}'$, $y_{pR}'$ in the above head angle equation, and steps 603, 604, and 606 are not performed In addition to IPD, or if absolute IPD is not determinable, another parameter may be determined referred to as the IPD-to-iris ratio which may be determined in the two-dimensional coordinates of a captured image of any eye in an image captured by sensor 111, or 111a or 111b (step 606). The relative IPD is the distance between the determined left and right pupil centroids ($x_{pL}$, $y_{pL}$) and ($x_{pR}$, $y_{pR}$) respectively, in the image in the case of the single sensor embodiment of FIG. 1 or by ($x_{pL}'$, $y_{pL}'$) and ($x_{pR}'$, $y_{pR}'$) for the two sensor embodiment of FIG. 2. The diameter of the iris ($D_L$ and $D_R$ as indicated in FIG. 4) is determined from the outer iris boundary in the image, such boundary' is determined when the iris is segmented from image; such segmentation is described, for example in U.S. Pat. No. 5,291,560. The iris diameter represents a virtual line from one side of the outer boundary through the iris centroid to the outer side of the outer boundary, which will provide two pixel positions along the outer boundary, the distance between them being the iris diameter. The relative IPD divided by the iris diameter is the IPD-to-iris ratio. Preferably, the diameters of both the right and left irises are calculated and then averaged to provide an average iris diameter for the subject, which is then used with the determined relative IPD to calculate an IPD-to-iris ratio in step 606.

In typical iris imaging systems, the iris which has an actual diameter of about 12 mm has a diameter of about 240 pixels in image coordinates. Therefore the pixel size, in object space, is about 0.05 mm. An integrodifferential operator, such as described in U.S. Pat. No. 5,291,560, or Hough transform, as described in earlier cited O'Gorman et al., p. 182, can be used to find the coordinates of the pupil center to subpixel accuracy. Since the distance between the pupil centers of a human ranges from 52 to 72 mm for an adult, taking 62 mm as the average, it is possible to determine head angle with an error no greater than $\tan^{-1}(0.05/62)=0.046$ degrees (2.76 arc-min). Once the head angle has been determined to be some angle θ, the iris image can be rotated about the iris or pupil center through an angle −θ, aligning the interpupillary line with the horizontal axis of the imaging system. If both the enrollment and recognition image are rotated to produce this alignment of the interpupillary line, no relative rotation will exist between the enrollment template and the recognition template. Typical iris template generation methods, such as that described in U.S. Pat. No. 5,291,560, may be used to encode iris texture with an angular resolution of approximately 1 to 2 degrees. Therefore the present invention has more than sufficient accuracy to eliminate the need to search over multiple rotation angles as described in U.S. Pat. No. 5,291,560. The rotation of iris images to remove all or substantially all head tilt is described at steps 905 and 906 of FIGS. 9A-D.

Referring to FIGS. 9A-D, flow charts are shown of the iris recognition processes in an iris identification system having the dual sensor iris capture device 100 of FIG. 2 having been previously calibrated using the calibration target. As stated earlier, such processes may occur at processors 113 in iris capture device 100 and/or in computer system 124. The iris capture device 100 captures left and right eye images (step 901 and 902). The pupil and iris boundaries and eyelids in each image are then determined (step 903 and 904). Identification of the pupil and iris boundaries in a given iris image may be as described, for example in U.S. Pat. No. 5,291,560. For each left and right eye image, an image of the annular iris region is extracted (i.e., segmented) in accordance with the determined boundaries, and then each segmented image is rotated by head angle −θ, determined earlier at FIG. 6, which rotates each image in a direction to all, or substantially, remove head tilt from each image, and the resulting image is normalized into polar coordinates in a rectangular image (fixed dimension) at steps 905 and 906. If the head tilt angle is below a threshold level, rotation of the segmented iris images may not be needed and is not performed. When single sensor iris capture device 100 of FIG. 1 is used, steps 901 and 902 are combined into a single step since a single image containing both eyes of the subject person is captured and later used in steps 903 and 904.

Optionally, the two-dimensional pixel positions in the left and right eye images captured by sensors 111a and 111b of FIG. 2 (or the image sensor 111 of FIG. 1 if calibration was performed) may be transformed into object space coordinates to correct for optical distortion, if present, and such corrected images then subsequently used by steps 903-906.

FIG. 11A shows the normalization of an annular iris image into a polar iris image. For example, an image 1100 may be captured by sensor 111a or 111b, or part of an image captured by sensor 111. This image 1100 contains the details of a single human eye as two dimensional pixels having gray-scale values, including the upper and lower eye lids, 1108 and 1109, respectively, and iris area 1102. The iris area 1102 is defined by an inner circular border 401 that is the boundary of the iris and pupil of the subject. The outer iris border is defined by the outer extent of the iris boundary 1107 and any occlusions arising from the upper and lower eyelids, 1108 and 1109, respectively. To convert the details contained within the iris area 1102 into a template, a zero angle line 1101 is defined by convention and the iris data within an annular area defined by an inner radius $r_i$ 1105 and an outer radius $r_o$ 1106 is extracted. The data is masked based upon any occlusions present (such as part of the eye lids or reflections) and the radial coordinate r 1111 of a data point 1110 is converted to a normalized radial coordinate $\hat{r}$ defined by $$\hat{r}(r) = \frac{r - r_i}{r_o - r_i}.$$

In this manner, each data point on the iris may be expressed by a radial coordinate $\hat{r}$ and an angle θ, such that the circular iris data is converted to a rectangular data block 1104, see FIG. 11B, where the y-axis is the normalized radial coordinate $\hat{r}$ and the x-axis is the angular dimension θ as defined in FIG. 11A. Thus each row of the normalized image represents a radius between the inner and outer circular borders of FIG. 11A, and each column is a different angle around the iris. Such normalization of iris images is also described in International PCT Patent Publication No. WO2005/11958181.

In FIG. 9A, after steps 901-906 the left and right normalized iris images are used to generate iris templates and masks (steps 907 and 908). Each template represents a binary encoding of the a normalized iris image, and the mask represent a map showing the areas of the template which do not represent that particular iris. The conversion of normalized iris images used to generate iris templates may be the same as described by U.S. Pat. No. 5,291,560, by using Garbor wavelets, but also the conversion may use Daubechies wavelets as described by U.S. Pat. No. 7,302,087, or discrete cosine transformations as described in European Patent Application No. 05747352.2, filed Jun. 1, 2004. The left and right iris templates and masks represent identification data characterizing the left and right iris images. Each iris mask indicates areas of the template where the iris image was obscured, such as by eyelids or reflections. and therefore these areas should not be used for matching.

The database 125, which may by way of example be flash memory, a hard drive or optical drive, stores identification data, i.e., template, of left and right iris of people enrolled in the identification system. At steps 909 and 910, comparative search occurs with respect to the left and right iris template from steps 907 and 908, and left and right iris templates stored for subjects in the database 125. Also stored for each left and right iris template in the database 125 is an associated mask indicating areas of their respective iris template which should not be considered when compared to another template. Thus, each comparison of a template of an acquired image and a stored template, areas of their respective masks in either or both images are not compared. The comparison of templates may also be performed as described in U.S. Pat. No. 5,291,560, but other template matching may be performed. Since the left and right iris images used to generate identification data (i.e., templates) stored in the database and the templates determined from left and right iris images presented for identification are all with zero or substantial zero head tilt, the matching of two templates with each other requires no relative rotation, or if needed, one or two relative rotation with respect to each other to obtain the desired precision.

Each comparison at steps 909 and 910 results in a match score, which are generated independently for the left and right iris images. A match score for a given iris provides a measure of the quality of match of the captured iris images at step 901 or 902 with one of enrolled iris images in terms of their respective templates without consideration of masked areas. Scoring of a match of two templates may be by use of Hamming distance, as described U.S. Pat. No. 5,291,560. For example, a score may represent equal comparison of bit pairs of the two templates being compared that do not match divided by total number of pair comparisons made. After all the comparisons are completed, at step 911 all left iris comparison resulting in a score above a predetermined threshold, represent a match, and at step 912 all right iris comparison resulting in a score above a predetermined threshold, represent a match. Thus the left and right irises are matched independently, and may use the same or different score thresholds. In the identification process of FIG. 9A, information from the left and right iris images are not combined or coordinated.

In FIG. 9B, steps 901-910 are the same as in FIG. 9A, but instead of steps 911-912, the match scores generated by the left and right iris images are combined at step 913. By way of example, the match scores may be combined using maximum likelihood techniques, such as described in Nandakumar, K., Chen, Y., Dass, S. C., and Jain, A. K., "Likelihood Ratio Based Biometric Score Fusion", *IEEE Transactions on Pattern Analysis and Machine Intelligence*, Vol. 30, No. 2, pp. 342-347, February 2008, and a combined or composite match score generated. This match score is then compared to a predetermined threshold at step 914 to reach a match decision.

In FIG. 9C, steps 901-908 are the same as in FIG. 9A-9B, but instead of steps 911-914, the two templates and masks from steps 907 and 908 are combined into a single composite template containing information from both irises (step 915). By way of example, if each individual template consists of an i×j array of values and each mask a k×l array of values, the two templates could be concatenated to produce a i×2*j template array and a k×2*l mask array. At step 916 this composite template is compared to previously enrolled composite templates to generate a match score, which is compared to a threshold at step 917 to reach a decision. This match score comparison at step 917 may or may not be identical to those used at steps 911, 912, and 914, depending on the similarity of scale among the various match scores. To enable step 916, database 125 stores identification data in the form of composite templates of the right and left irises for facilitating comparison with the presented composite template in which comparison is carried out in areas where the corresponding mask value for both the database template and the presented template have a particular value, such as one, but is not carried out in other areas where the mask for at least one of the database template or the presented template has a different value, such as zero. In FIG. 9D, steps 901-906 are the same as in FIG. 9A-9C, but instead of steps 911-915, the two normalized left and right images from steps 905 and 906 are combined to form a composite two-eye normalized iris image (step 918). By way of example, if each image is an m×n array of pixel intensity values, the right and left images could be concatenated to produce a single m×2*n image array in which the left and right iris images appear side-by-side. At step 919 a composite template is generated from the composite iris image. This composite template has the same format as that generated at step 915 (FIG. 9C), so the comparison process at step 916 and the match process at step 917 are identical to those in FIG. 9C. A different desired matching process in FIG. 9D may occur if the template format from step 919 is different and hence incompatible with that of FIG. 9C.

Referring to FIGS. 7A and 7B, the detection of a patterned contact lens using the two pupil centers and the line between them is illustrated, as may be carried out by a software program operating the processor(s) 113 in either housings 100a or 100b, or the computer system 124. For purposes of illustration, left and right eye images of the subject person are shown in FIGS. 7A and 7B; however a single image with both eyes may also be used. In FIG. 7A, the pupil centers and the interpupillary line are determined in object space, and the head angle is determined as described earlier. The iris image in the left image 701 is rotated as described above to correct for head angle, and is then processed to generate an iris template. It is assumed that the eye contains a contact lens with outer boundary 703. This contact lens contains, by way of example, a radial feature 704 positioned at an angle $\phi_1$ relative to the interpupillary line 705. A subsequent set of images is captured as shown in FIG. 7B and processed as before to determine the pupil centers, interpupillary line, and head angle, and a template is generated from the left image. In this second image the same radial feature 706 is now positioned at an angle $\phi_2$ relative to the interpupillary line 707. This template can be matched against the template generated from the first image, shown in FIG. 7A. The two left image templates should match; if they do not, then relative rotations of the two images can be tested to see if a match occurs when relative rotation between the first and second left eye images is assumed to exist. If such a match occurs it indicates that $\phi_1$ is not equal to $\phi_2$ because the iris rotated, while the head did not, indicating that the iris pattern must be printed on a contact lens. This patterned contact detection process may be performed as part of the iris identification process of FIGS. 9A-D by processing multiple images having the eye(s) of a person captured at different times prior to image normalization and/or comparison searches. As part of the capture sequence, the subject may be induced or required to blink as blinking can shift and rotate contact lenses. By capturing iris images before and after blinking and checking for iris rotations inconsistent with head tilt angles, a spoof is detectable.

For certain applications of the iris identification system, software in the device 100 or in computer system 124 (if present) may provide for weighted contact spoof detection. First, the subject is directed by the system (or operator) to purposely tilt his or her head at a substantial angle and may be additionally requested to blink at the time of image capture, such that if the iris template(s) of the captured iris image(s), which is rotated by the angle at which the subject is directed or determined to have tilted his or her head, when compared to the subject's reference iris template matches (i.e., such match being sufficient to indicate a positive correlation) at a relative angle significantly different (i.e., greater than a threshold) from the subject's actual head tilt angle, then the system concludes that the subject is wearing weighted spoof iris contacts and the subject is an imposter. The difference between the expected and observed head tilt may not be zero even in the absence of a spoof contact lens, because of the phenomenon of cyclotorsion, a rotation of the eye about its anteroposterior axis when the head is tilted or the subject changes from a supine (lying down) to a sitting position. Measurements of cyclotorsion between supine and sitting positions are reported in Chang, J., *Cyclotorsion during laser in situ keratomileusis*, Journal of Cataract and Refractive Surgery, 34(10):1720-1726, 2008. Mean rotation of the eye was 2.18 degrees and in some subjects was as high as 13.3 degrees. Therefore the observed difference between the expected and observed head tilt, based on the comparison of iris rotation to head angle, should be greater than a threshold, such as at least 5 or 10 degrees, in order to conclude that a spoof contact lens may be present. Spoof detection preferably entails first shifting the captured template(s) (equivalent to rotating the image of the iris) through a rotational angle about the amount which the subject is directed or determined to have tilted his or her head. The shifted captured iris template is compared to the iris template in the database 125 and if no match is found, the system analyzes the match scores for rotation angles successively further from the initial rotation until a match is found or all reasonable rotational angles are analyzed. If a match is found at a relative angle that differs significantly from the angle at which the subject actually tilted his or her head with respect to the iris capture device, then a fake iris spoof contact lens is detected and the subject is an imposter. In other words, the iris image was determined to be rotated relative to the interpupillary line by an amount larger than what can reasonably be explained by cyclotorsion, the conclusion is that the anomalous iris rotation is due to the presence of spoof contacts worn by the subject that have rotated from their normal position. The anomalous detected rotation may be the result of weighted spoof contacts which normally orient themselves correctly on the eye when the subject's head has minimal tilt angle but will orient relative to the direction of gravity and not the subject's head if the head is tilted. For example such head tilt may be at least 20 degrees, in which if the measured head tilt is less than 20 degrees, a spoof may be present. To assure that the subject rotates his or her head by an expected amount, a rotational mount having mechanical fixture(s) on which the subject's head rests may be provided having an upright position for normal iris capture and a tilt position to provide a desired head tilt for spoof detection. The amount of tilt with respect to the iris capture device at the tilt position is predetermined by the iris identification system, or may be periodically changed or randomly selected for different subjects, by the system. Other means for assuring the amount of subject head tilt may also be used, such as visual references, aiming light(s), or narrow angularly viewable elements, such a graphics, text, or image, which the subject must tilt his or head the desired amount to view.

Since the degree of eyelid occlusion is usually very similar in the right and left eyes, information derived from both eyes can be compared and correlated to achieve more accurate segmentation. Segmentation determines the portion of the eye image comprising the iris and the annular ring that surrounds the pupil. The iris can be partially occluded by the eyelids, in particular the upper eyelid. Determination of the boundaries between the iris and the upper and lower eyelids is important to achieving accurate recognition performance, since for best performance the iris matching must be based only on iris texture features, and not on other features, such as eyelids, which may be similar for images from different eyes. Detection of eyelids may be difficult due to marginal contrast between iris and eyelid, or the presence of eyelashes that may obscure the boundary between iris and eyelid. The involuntary nerve stimuli that cause the eyelids to move, such as when the eye blinks, affect both the left and right eyelids in the same way. Therefore, information about eyelid position in one eye image can be correlated with the same information in the other eye image to improve the performance of eyelid segmentation, as shown in FIG. 8.

FIG. 8 illustrates the use of images from the dual sensor iris capture device 100 of FIG. 2 to improve the performance of eyelid-finding at steps 903 and 904. The left image 701 contains an upper eyelid 801 while the right image 702 contains an upper eyelid 802. The detection of eyelids searches for the eyelid boundary within a search region designated as 803 in the left image and 804 in the right image. Eyelid detection may be performed by detecting edge points followed by spline fitting (see for e.g., earlier cited O'Gorman et. al., pp. 217-219) or Hough transform (see O'Gorman et al., pp. 182-185), techniques. The object-plane positions $(x_{pL}', y_{pL}')$ and $(x_{pR}', y_{pR}')$ of the left and right pupil centers provide a common landmark for the eyelid searches. Since eyelid position is usually nearly identical in right and left eyes, the search processes for the left and right eyes can be coordinated and evidence of eyelid position from the left and right images can be combined to improve the accuracy of the eyelid location in both images. For purposes of illustration, left and right eye images of the subject person are shown in FIG. 8, however a single image with both eyes may also be used. The matching of eyelid position may take place at step 903 and 904 of FIGS. 9A-D, and if eyelid locations are outside a matching tolerance, then new image(s) of the eyes are captured by dual sensor iris capture device 100, and steps 903 and 904 are repeated.

Enrollment of a person in the iris identification system having device 100 is shown in FIG. 10. First, the right and left iris images are captured by iris capture device 100 at step 1001 in a single image (FIG. 1) or in different images (FIG. 2) captured at or approximately at the same time. At step 1002, the right and left iris images are segmented to locate the pupil and iris boundaries and eyelid positions, as in step 903 and 904 with respect to each eye. The left and right pupil centroids are determined at step 1003 and transformed from image coordinates to the common object plane coordinate system at step 1004, as in steps 601-604 (FIG. 6). If a single image captures both the left and right eyes and absolute IPD information is not to be used, step 1004 is not required. The pupil centroids are used to calculate head tilt and IPD at 1005, such as described earlier. If IPD is not needed, then such is not determined at step 1005. Optionally at step 1005, an IPD-to-iris ratio may be determined for each eye, as described earlier. Preferably, the diameters of both the right and left eyes are calculated and averaged to arrive at an IPD-to-iris ratio. At step 1006, the left and right iris images are remapped to the rotational position that corresponds to zero or substantially zero head tilt, as described at step 905 and 906 (FIG. 9A-D). The template generation process is performed at 1007, including extraction of the normalized polar image, calculation of the iris template, and calculation of the iris mask for each eye, as described at step 905-908. Finally at step 1008, the iris templates, iris masks, and optionally the iris images, and IPD and/or IPD-to-iris ratio if determined, are stored as identification data in database 125 (FIG. 2A) along with other personal information, such as name, photograph of the individual captured at time, or other types of information typical of iris identification or recognition systems.

The identification data stored in the database 125 may be partitioned in accordance with IPD values or ranges, so the newly enrolled identification data is stored accordingly by IPD. During identification, a subject's irises can be characterized by their IPD to facilitate faster searches and spoof detection.

When at identification and enrollment, an IPD-to-iris ratio is determined in which the relative or absolute IPD is scaled to the iris outer diameter (or scaled to the average iris outer diameter of both eyes if both are determined to be live). Such iris outer diameter may be determined in accordance with object coordinates of pixels located along the outer iris boundaries found at steps 903 and 904, and IPD and/or IPD-to-iris ratio may be used as an additional matching parameter when comparative searching in FIGS. 9A-D, where at time of enrollment, the iris outer diameter that may be determined in accordance with object coordinates of pixels located along the outer iris boundaries found at step 1002 is stored along with other identification data for each person when added to the iris identification system. The advantage of the use of an IPD-iris ratio for the classification of a subject's iris is that such a ratio is dimensionless and independent of image magnification. For iris capture devices that operate at a fixed distance between the imaging system and the pupil, the advantage of the IPD-iris ratio to raw IPD is not significant. However, for an optical system that uses a rough range finder and some means of an autofocus mechanism to bring the object in focus or an optical system that incorporates wavefront coding or a similar technology such that the depth of focus of the optical system is significant, the consequence is that the magnification of the captured iris image can vary significantly. In this case the magnification independence of the IPD-iris ratio allows for more accurate classification of the subject's iris during enrollment.

Upon subsequent 1:N identification, iris matching need only match said subject's iris with other irises in the database that have the same IPD or IPD-iris ratio (within a small error range). Additionally the use of IPD or IPD-iris ratio information deters spoof attempts wherein the subject is trying to assume the identity of a person already enrolled in a particular iris database. Due to the two-eye capture, a subject attempting to spoof the system with a set of fake iris contact lenses must have the same IPD or IPD-iris ratio as that of the person he or she is trying to imitate.

Although head tilt correction is described above utilizing predefined ocular features, such as pupil or iris centers of two eyes of a person, optionally head tilt angle may be determined using a single image of the eye. In FIG. 12, an example of an image 1200 of a single eye is shown that may be captured with a single camera of iris capture device 100 represented in FIG.

2, or iris capture device of FIG. 1 in which sensor 111 and optics 108 are sized to capture an image of a single eye, rather than two eyes. In image 1200 the captured eye image comprises a pupil 1103, an iris 1102, upper eyelid 1204, lower eyelid 1205, nasal canthus 1210, and temporal canthus 1211. Processor(s) in the iris capture device or the computer system coupled thereto may detect locations of eye corners and eyelids in the captured image as described, for example, in Uzunova, V. I., An eyelids and eye corners detection and tracking method for rapid iris tracking, Master's Thesis, Otto-von-Guericke University of Magdeburg, Department of Computer Science, Magdburg Germany 2005, pp. 31-37. The rotation of the eye may be derived by connecting a virtual line 1203 between features 1201 and 1202 which are the nasal and temporal corners of the eye, respectively. The line 1203 connecting these features is rotated by an angle $\theta_r$ relative to a horizontal line 1212 defined by one of the axes of the rectangular image 1200. By way of example, the iris rotation may be defined by $\theta_r$ or it may be defined by a value $\theta_r - \Delta$, where $\Delta$ is the nominal eye-corner-to-corner tilt angle present in an eye when there is zero head tilt angle.

Considering the capture of a single image of the eye from which the iris image is segmented, steps 901, 903, 905, 907, and 909 of FIG. 9A, may be performed as described earlier where the single image is of the left eye image capture, except that the extracted (or segmented) iris image is not rotated based on a virtual line between pupil centers, but rotated in accordance with an angle that aligns a line through the corners of the eye with a dimension associated with zero tilt, such as horizontal axis of the sensor array 1212, to remove or substantially remove head tilt. The same occurs at enrollment to remove or substantially remove head tilt from an iris image prior to generating of the template and mask. Rather than rotating the extracted iris image when head tilt is detected, the extracted iris image may be first normalized and generated into an iris template, which may then be rotated in accordance with the determined angle, rather than rotating the whole extracted iris image. As stated earlier, a mask is also generated when an iris template is generated; such mask is also rotated by the same angle when the iris template is rotated such that both iris template and mask have zero or substantially zero head tilt when stored as a reference for enrollment or used for identification or verification. Although FIG. 12 and this example utilizes the left eye of a person, it may similar be applied to the right eye. Spoof detection described earlier for detecting a weighted iris contact spoof may also be performed for a single iris image by the detection of anomalous iris rotation when a subject substantially tilts his or her head.

Optionally, instead of rotating the segmented iris image by the angle between a line extending through eye corners and the horizontal axis of the sensor array, a predetermined tilt condition of the canthi from the horizontal axis is used. For example, if such predetermined canthi tilt condition represents canthus line tilt angle of 5 deg, then when capturing a subject with one eye image at a time, if a 6 deg tilt of the canthi line from the horizontal axis is determined, then the segmented iris image is rotated by −1 deg to align the canthi line to the 5 deg angle, and the rotated iris image and/or its associated template is either stored in the database for enrollment, or used for comparison.

The above describes use of the horizontal axis of the image for the single sensor iris captured device in determining an angle between a virtual line in a single image of one eye or two eyes; however, the vertical axis may instead be used, or another dimension defined as relating to a zero or known tilt condition of features in the single image.

At enrollment in the database of an iris identification system, the segmented iris image may be rotated to remove head tilt when stored in a database of enrolled iris images, such as in terms of iris templates. When the same software is used for capturing an iris image for identification, the iris image may be rotated, and such rotation may occur using the annular iris image or the normalized iris image. However, by incorporating this method in software for operating the identification system utilizing a single iris for identification, such as in U.S. Pat. No. 5,291,560, can reduce the number of relative rotations between the reference template and the template of a subject's iris image to the one matching determined angle $\theta_r$ in the iris image, as shown for example in FIG. 12. Reducing the number of relative rotations necessary to compare each reference template in the database and the template of a subject's iris image to one (or two if necessary) in arriving at a score for the amount of match between comparison, greatly reduces the time in U.S. Pat. No. 5,291,560 for identification of a subject.

Preferably, optical distortion by optical systems 108a and 108b on their respective sensors in images can be accounted by the transformation of two-dimensional pixel positions and two dimensional object coordinates for iris capture device 100 of FIG. 2, and also in iris capture device 100 of FIG. 1 when calibration is performed to correct when such optical distortion of optical system 108 would negatively impact desired accuracy of head tilt correction, IPD or IPD to iris ratio. However optical system 108 may purposefully provide distortion to reduce the length (along the optical axis) and/or size of the optical system, and thus reducing the size (and weight) of housing, such as shown in single sensor iris capture device 100 of FIG. 13. The iris capture device of FIG. 13 is similar to the iris capture device of FIG. 1, except that the distance $L_1$ between a housing 100c and the subject's eyes 101a and 101b has been reduced. By reducing the distance $L_1$ and also requiring that the housing 100c be thin (i.e., length $L_2$ is reduced) requires that the optical system 108 operate across a large field-of-view. Such wide-field-of-view optical systems, e.g., fish-eye lens(es), have large geometric distortions. By way of example, an on-axis imaging system operating at ±5° may have geometric distortions less than 1%. However, an optical system operating at ±30° may have optical distortions of 5 to 10%. Such high distortions can affect the accuracy with which an iris template matching algorithm can perform matches if one of the iris templates in the matching was obtained from an uncorrected distorted iris image. As stated earlier, to correct images with high geometric distortions, one increases the number of points $p_i$ that are used in the calibration of iris capture device 100 of FIG. 1. The higher the geometric distortion that must be corrected, the more points $p_i$ that must be analyzed. However, distortion due to such wide angle distortion may not be sufficiently correctable using transformation of a rotation and scaling A and translation vector b, and a more complicated image correction may be needed, such as that described for example in U.S. Pat. No. 7,324,706.

Although head tilt is preferably corrected at iris comparison and at enrollment, optionally the left and right iris images are not rotated, but the head tilt angle determined using image(s) of both eyes or a single eye image is recorded with iris template information in the identification system database at time of enrollment. Upon comparison matching to other iris templates in a database, the head tilt angle is used to provide iris rotation information to accelerate matching. For example, at the time of processing of a set of recognition images, the rotation information may be used to compensate for the difference in head tilt between the enrollment and recognition images, as in steps 905 and 906 of FIGS. 9A-D. Further, the head tilt angle information is used in order to help detect a spoof consisting of a fake iris contact as such a fake iris will naturally rotate in the eye, while a real iris will not.

In addition to identifying a subject, the system may be used for verification of the identity of a particular subject. For verification, the steps of FIGS. 9A-D are performed, but with the comparison and matching steps being applied to the iris template(s) of the subject captured by the iris capture device and the iris template(s) and mask(s) for that particular subject, such iris templates and their respective mask(s) being selected by processor(s) 113 or computer system 124 (FIG. 2A) from the database 125 of identification information. The selection being in accordance with subject information (e.g., badge ID, password, or some other token) inputted to the user interface or a reader, coupled to the computer system 124, for the subject to be verified, where the subject information inputted is matched to field(s) in record(s) stored in the database to access associated, stored iris template(s) and mask(s). If the comparison yields a match score above a threshold then the particular subject's identify is confirmed. Optionally if there is no verification match, the software operating on the processor(s) of the iris capture device or the computer system coupled thereto, shifts the captured template (equivalent to rotating the image of the iris) through a series of translations, each time comparing the shifted template to the iris template in the database. If after shifting the templates one or more times a match is found, then an imposter is detected. However, depending on the type of comparative matching performed, an additional check may be performed after a match is found to determine whether the rotational offset required to arrive at a match is greater than a threshold level to better assure that the subject is indeed an imposter. The reason for shifting the template in verification is to determine why the iris matching for verification might not be working when the subject has provided a correct badge ID, password, or some other token, and avoid having a human, such as a security guard, intervene to override the system and personal verify the subject's identity, when in fact a spoof contact lens is being perpetrated. Less preferably, this optional spoof detection for verification may also take place for identification after each unsuccessful match attempt between an iris template from the database and the iris template of the captured iris image. Such is less preferable, since it increases the number of comparison attempts required and thereby increases the amount of time needed to compare the captured template to each reference template from the database. Verification and such spoof detection may also be performed for single iris images after correcting the iris template for head tilt with respect to the template of the subject in a database. Other spoof detection described earlier for identification may also be used for verification, such as in connection with FIGS. 7A-B for the two eye images, and/or detection of a weighted iris spoof contact lens by directing subject to tilt his or her head.

From the foregoing description, it will be apparent that there have been provided an improved apparatus and method for an iris imaging and iris identification system using such apparatus. Variations and modifications in the herein described apparatus, method, and system in accordance with the invention will undoubtedly suggest themselves to those skilled in the art. For example, the eyes have been described herein as the eyes of a human subject; the eyes may be of animals as well, such as horses, for enabling iris identification. Accordingly, the foregoing description should be taken as illustrative and not in a limiting sense.

The invention claimed is:

1. An apparatus for capturing images of the eyes of a subject for use in an iris identification system, said apparatus comprising:
   one or two sensor arrays which capture a single image or two images, respectively, representing the different eyes of a subject captured at or approximately at the same time, in which when a single image is captured having both eyes of a subject a dimension extends in said single image associated with zero head tilt, and when two images are captured each having a different eye of the subject each of said sensor arrays are calibrated along a common plane to enable locations in images of different eyes of a subject captured by the sensor arrays to be related to coordinates along said common plane, and a dimension along said common plane is associated with zero head tilt;
   means for determining a location of a predefined feature associated with each of the different eyes of the subject present in said single image or two images, in which when two images are captured said location of said predefined feature is determined in each of the images in coordinates along said common plane;
   means for determining an angle between a virtual line extending between the two eyes of the subject, in which said virtual line extends through said location of the predefined feature of each of the different eyes of the subject in said single image or two images, and said dimension associated with zero head tilt along said single image or said common plane, respectively;
   means for segmenting left and right iris images from said single image or two images of the different eyes of the subject; and
   means for rotating said segmented left and right iris image in accordance with said angle to substantially remove head tilt when present and thereby provide left and right iris images with substantially zero head tilt.

2. The apparatus according to claim 1 further comprising a plurality of illumination sources for illuminating said eyes of the subject when said single image or two images are captured by said one or two sensor arrays, respectively.

3. The apparatus according to claim 2 further comprises for each of said one or two sensor arrays an optical system for focusing onto the sensor array reflected light from said eyes when said eyes are illuminated.

4. The apparatus according to claim 1 wherein said means for determining a location of a predefined feature further comprises:
   means for determining boundaries of pupil and iris for each of said different eyes in said single image or two images, in which said location of the predefined feature associated with each of the different eyes of the subject present in said single image or two images is determined with respect to said determined boundaries.

5. The apparatus according to claim 1 wherein said predefined features represent the center of pupil or iris.

6. The apparatus according to claim 1 wherein when two sensor arrays are present said two sensor arrays are calibrated along said common plane representing a target form having features imaged by said two sensor arrays to provide two calibration images in which features on calibration images are calibrated to known coordinates along said target form to enable locations in images of different eyes of a subject captured by the sensor arrays to be related to coordinates along said common plane.

7. The apparatus according to claim 1 further comprising means for determining a distance between the location of said predefined features associated with each of the different eyes of the subject, said predefined features represent the center of the pupil or iris of each of the different eyes of the subject, wherein said distance defines an interpupillary distance (IPD) of the subject.

8. The apparatus according to claim 7 further comprising:
a database storing identification data associated with iris data representative of at least other left or right iris images of a plurality of subjects with substantially zero head tilt and IPD of said plurality of subjects; and
means for identifying the subject utilizing one or both said left and right iris images having substantially zero head tilt and said IPD of the subject in accordance with said database.

9. The apparatus according to claim 8 wherein said database is partitioned into different values or ranges of IPD, and said identifying means utilizes said iris data of the partition in said database having a value or range related to said value representing the IPD of the subject.

10. The apparatus according to claim 1 further comprising:
a database storing identification data associated with at least iris images of a plurality of subjects with substantially zero head tilt; and
means for generating identification data for the subject for addition to said identification data stored in said database utilizing one or both said left and right iris images having substantially zero head tilt.

11. The apparatus according to claim 1 further comprising:
means for generating a left template and a right template representative of said left iris image and said right iris image, respectively, of the subject having substantially zero head tilt;
a database storing identification data representing the left and right templates generated from left and right iris images, respectively, of a plurality of subjects with substantially zero head tilt; and
means for identifying the subject by comparing left template of the subject and each of the left templates stored in said database to provide for each comparison a score representative to the amount of match of the left iris, and comparing the right template of the subject and each of the right templates stored in the database to provide for each comparison a score representative to the amount of match of the right iris, and determining when one said plurality of subjects represents said subject in accordance with said score representative of said left iris and said score representative of said right iris.

12. The apparatus according to claim 11 wherein means for identifying the subject further combines said score representative of said left iris and said score representative of said right iris to provide a composite score, and said combined score is utilized to determine when one said plurality of subjects represents said subject.

13. The apparatus according to claim 1 further comprising:
means for generating a left template and a right template representative of said left iris image and said right iris image, respectively, of the subject having substantially zero head tilt, and combining said left template and said right template to provide a composite template;
a database storing identification data representing composite templates of left and right templates generated from left and right iris images, respectively, of a plurality of subjects with substantially zero head tilt; and
means for identifying the subject by comparing composite template of the subject and composite templates stored in said database to provide for each comparison a score representative to the amount of match, and determining when one said plurality of subjects represents said subject in accordance with said score.

14. The apparatus according to claim 1 further comprising:
means for generating a composite image of said left and right iris images having substantially zero head tilt of the subject;
means for generating a template representative of said composite image;
a database storing identification data representing the templates generated from composite left and right iris images, respectively, of a plurality of subjects with substantially zero head tilt; and
means for identifying the subject by comparing template of the subject and each of the templates stored in said database to provide for each comparison a score representative to the amount of match, and determining when one said plurality of subjects represents said subject in accordance with said score.

15. The apparatus according to claim 1 further comprising one or more processors for enabling said location determining means, angle determining means, segmenting means, and rotating means.

16. The apparatus according to claim 15 further comprising:
a housing having at least said one or two sensor arrays, and a plurality of illumination sources for illuminating the eyes of the subject when said single or two images are captured; and
a computer system having said processors for receiving said single image of two imaged captured by said one or two sensor arrays.

17. The apparatus according to claim 15 further comprising:
a housing having at least said one or two sensor arrays, and a plurality of illumination sources for illuminating the eyes of the subject when said single or two images are captured; and
a computer system for receiving said single image of two images captured by said one or two sensor arrays, wherein said one or more of processors are located in said housing and one or more other of said processors are located in said computer system.

18. The apparatus according to claim 15 further comprising a housing having at least said one or two sensor arrays, and a plurality of illumination sources for illuminating the eyes of the subject when said single or two images are captured, and said processors.

19. The apparatus according to claim 1 further comprising:
means for determining a distance between the location of said predefined features associated with each of the different eyes of the subject in said single image or two images, said predefined feature represent the center of the pupil (or iris) of each of the different eyes of the subject; and
means for determining the outer diameter of the left iris and right iris in said single image or two images; and
means for determining a first ratio of said distance to said outer diameter of the left iris, and a second ratio of said distance to said outer diameter of the right iris, and for combining said first and second rations to provide an IPD-to-iris ratio for the subject.

20. The apparatus according to claim 19 further comprising:
a database storing identification data associated with iris data representative of at least other left or right iris images of a plurality of subjects with substantially zero head tilt and IPD-to-iris ratio of said plurality of subjects; and means for identifying the subject utilizing one or both said left and right iris images having substantially zero head tilt and said IPD-to-iris ratio of the subject in accordance with said database.

21. The apparatus according to claim 20 wherein said database is partitioned into different values or ranges of IPD-to-iris ratio, and said identifying means utilizes said iris data of the partition in said database having a value or range related to said value representing the IPD-to-iris ratio of the subject.

22. The apparatus according to claim 20 further comprising means for identifying a fake iris by performing said location determining means and said angle determining means two or more times to provide two or more determined angles with respect to different ones of captured single image or two images, in which the subject blinks or tilts between said different successive ones of captured single image and two images, in which said iris is fake when two or more of said two or more determined angles are substantially different from each other.

23. The apparatus according to claim 1 wherein said segmenting means further comprises means for determining boundaries of pupil and iris, and location of the upper eyelid, for each of said different eyes in said single image or two images, in which said segmented left and right iris images represent the portion of said single image or one of said two images between the boundaries of the pupil and iris of the left and right eye, respectively, not occluded by said eyelid, and when the position of the upper eyelid with respect to the iris in each of said eyes is not substantially the same, said one or two sensor arrays capture another of the single image or two images and at least said segmenting means is operative upon said another of the single image or two images.

24. An apparatus according to claim 1 wherein when only one of said one or two sensor arrays is present, the sensor array is calibrated along a common plane to enable locations in images of different eyes of a subject captured by the sensor array to be related to coordinates along said common plane, and said determining location means is operative upon the single image for determining a location of a predefined feature associated with each of the different eyes of the subject present in said single image in coordinates along said common plane, and said determining angle means determines an angle between a virtual line extending between the two eyes of the subject, in which said virtual line extends through said location of the predefined feature of each of the different eyes of the subject in said single image, and said dimension associated with zero head tilt along said common plane.

25. The apparatus according to claim 1 further comprising:
means for generating one or more iris images having substantially zero head tilt of the subject;
means for generating one or more first templates representative of said one or more iris images;
means inputting subject information and selecting from a database, which stores at least templates of a plurality of subjects with substantially zero head tilt, one or more second templates stored in said database associated with said subject information; and
means for verifying the identity of the subject by comparing said one or more first templates with said one or more second templates to determine a score representative of the amount of match, and determining when said subject is verified in accordance with said score.

26. The apparatus according to claim 25 further comprising:
means for rotating one or more first templates and said one or more second templates with respect to each other to determine a match between said one or more first templates and one or more second templates match indicating that said subject is an imposter when said subject is not verified by said verifying and determining means.

27. A device for capturing images of the eyes of a subject for use in an iris identification system, said apparatus comprising:
first and second sensors which capture images at or approximately at the same time different eyes of a subject when each of said different eyes is presented to different ones of said first and second sensors, in which images captured by said first and second sensors are calibrated along a common plane to enable locations in images of different eyes of a subject captured by said first and second sensors to be related to coordinates along said common plane, and a dimension along said common plane associated with zero head tilt;
means for determining a location of a predefined feature in each of the images of the different eyes of a subject captured by said first and second sensors at or approximately at the same time;
means for determining an angle between a virtual line extending with respect to said location of said predefined feature in each of the images in coordinates along said common plane, and said dimension along said common plane associated with zero head tilt; and
means for segmenting left and right iris images from said images of the different eyes of the subject captured by said first and second sensors at or approximately at the same time, and rotating said segment left and right iris image in accordance with angle to substantially remove head tilt when present in said images.

28. A method for acquiring images of the irises of two eyes of a person comprising the steps of:
capturing a single image or two images using a one or two sensor arrays, respectively, representing the different eyes of a subject captured at or approximately at the same time, in which when a single image is captured having both eyes of a subject a dimension extends in said single image associated with zero head tilt, and when two images are captured each having a different eye of the subject each of said sensor arrays are calibrated along a common plane to enable locations in images of different eyes of a subject captured by the sensor arrays to be related to coordinates along said common plane, and a dimension along said common plane is associated with zero head tilt;
determining a location of a predefined feature associated with each of the different eyes of the subject present in said single image or two images, in which when two images are captured said location of said predefined feature is determined in each of the images in coordinates along said common plane;
determining an angle between a virtual line extending between the two eyes of the subject, in which said virtual line extends through said location of the predefined feature of each of the different eyes of the subject in said single image or two images, and said dimension associated with zero head tilt along said single image or said common plane, respectively;
segmenting left and right iris images from said single image or two images of the different eyes of the subject; and rotating said segmented left and right iris image in accordance with said angle to substantially remove head tilt when present in said left and right iris images.

29. A device providing images of the iris of two eyes of a subject for use in one of enrolling or identifying the subject in an iris identification system, said device comprising:
   one or two sensors for capturing one or two first images having the left eye and of the right eye of a subject captured at or approximately at the same time, wherein each of said one or two first images represents a two-dimensional array of pixels;
   a dimension with respect to pixels in said one or two first images which characterizes zero head tilt; and
   at least one processor, responsive to receiving said one or two first images, segments from said one or two first images a second and third images representing said right and left irises, respectively, viewable in said one or two first images, and rotates one or more of said second or third images to align predefined features present in said captured one or two first images along said dimension when said predefined features are substantially non-aligned along said dimension.

30. The device according to claim 29 wherein said at least one processor determines an angle between a virtual line extending through a location of the predefined feature of each of the different eyes of the subject in said one or two first images, and said dimension, said rotation by said at least one processor of said second and third images is in accordance with said angle to align predefined features present in said captured one or two first images along said dimension when said predefined features are substantially non-aligned along said dimension.

31. The device according to claim 29 further comprising a plurality of illumination sources for illuminating said eyes of the subject when said one or two first images are captured by said one or two sensors, respectively.

32. The device according to claim 31 further comprising for each of said one or two sensors an optical system for focusing onto the sensor reflected light from said eyes when said eyes are illuminated.

33. The device according to claim 29 wherein said at least one processor determines a location of each of the predefined features present in said one or two first images by determining boundaries of pupil and iris for each of said different eyes in said one or two first images, in which said location of the predefined feature associated with each of the different eyes of the subject present in said one or two first images is determined with respect to said determined boundaries.

34. The device according to claim 29 wherein each of said predefined features represents a center of a pupil or iris.

35. The device according to claim 29 wherein when two of said one or two sensors are present said two sensors are calibrated along a common plane representing a target form having features imaged by said two sensors to provide two calibration images in which features on calibration images are calibrated to known coordinates along said target form to enable locations in images of different eyes of a subject captured by the sensors to be related to coordinates along said common plane.

36. The device according to claim 29 wherein said at least one processor determines a distance between the location of said predefined features associated with each of the different eyes of the subject in accordance with said one or two first images, said predefined features represent the center of the pupil or iris of each of the different eyes of the subject, and wherein said distance defines an interpupillary distance (IPD) of the subject.

37. The device according to claim 29 further comprising:
   a database storing identification data associated with at least iris images of a plurality of subjects with substantially zero head tilt; and
   said at least one processor generates identification data for the subject for addition to said identification data stored in said database utilizing one or both said left and right iris images having substantially zero head tilt.

38. The device according to claim 29 further comprising:
   a database storing identification data representing the left and right templates generated from left and right iris images, respectively, of a plurality of subjects with substantially zero head tilt; and
   said at least one processor generates a left template and a right template representative of said left iris image and said right iris image, respectively, of the subject having substantially zero head tilt, and identifies the subject utilizing said identification data of said database and at least one of the left template and right template.

39. The device according to claim 29 wherein each of said one or two sensors is a sensor array.

40. The device according to claim 29 wherein said predefined feature represent the center of the pupil or iris of each of the different eyes of the subject, said at least one processor determines a distance between the location of said predefined features associated with each of the different eyes of the subject in accordance with said one or two first images, determines the outer diameter of the left iris and right iris in said one or two first images, and determines a first ratio of said distance to said outer diameter of the left iris, and a second ratio of said distance to said outer diameter of the right iris, and combines said first and second rations to provide an IPD-to-iris ratio for the subject.

41. An apparatus for determining head tilt angle using a single image of one or two eyes of subject comprising:
   a sensor for capturing an image of one or two eyes of a subject having two dimensions;
   means for determining two locations of predefined features in the image;
   means for determining an angle between a virtual line extending through said locations of the predefined features and one of said dimensions or a predetermined tilt condition from one of said dimensions.

42. The apparatus according to claim 41 further comprising:
   means for segmenting an iris image from said image; and
   means for rotating said iris image derived in accordance with said angle.

43. The apparatus according to claim 41 further comprising:
   means for segmenting an iris image from said image;
   means for generating an iris template representative of said iris image; and
   means for rotating said iris template in accordance with said angle.

44. The apparatus according to claim 43 wherein the head of the subject is substantially tilted when said image is captured, and said apparatus further comprising means for comparing said rotated iris template with another iris template associated with the subject to determine an angle at which said rotated iris template and said another iris template sufficiently matches to indicate a positive correlation, and wherein said angle when said match occurs is greater than a threshold than said subject represents an imposter.

45. The apparatus according to claim 41 wherein said image is of one eye of the subject and said predefined features represent nasal and temporal canthi.

46. The apparatus according to claim 41 wherein said image is of two eyes of the subject and said predefined features represent iris or pupil centers.

47. The apparatus according to claim 41 further comprising means for determining when said subject represents an imposter in accordance with said image.

48. An apparatus for use in one of enrolling or identifying a subject in an iris identification system, said apparatus comprising:
- a sensor for capturing an image of at least one eye of a subject;
- a dimension in said image which characterizes zero head tilt or a predetermined tilt condition; and
- at least one processor which at least determines an angle between a virtual line extending between two predefined features associated with the eye of the subject in said image and said dimension.

49. The apparatus according to claim 48 wherein one of said two predefined features represents an inner corner of the eye in the image, and the other of said two predefined feature represents an outer corner of the eye in the image.

50. An apparatus for use in one of enrolling or identifying a subject in an iris identification system, said apparatus comprising:
- one or two sensors which capture a single image or two images, respectively, representing the different eyes of a subject, and when two images are captured each has a different eye of the subject and are calibrated along a common plane;
- a dimension along said single image or along said two images along said common plane; and
- at least one processor which at least determines an angle between a virtual line extending through locations of two predefined features in said single image, or in said two images along said common plane, and said dimension, in which said two predefined features are each associated with a different one of the eyes of the subject.

51. The apparatus according to claim 50 wherein said one or two sensors are each a sensor array, and said dimension extends linearly along the sensor array of said one or two sensors.

* * * * *